US010669553B2

(12) United States Patent
Jiang et al.

(10) Patent No.: US 10,669,553 B2
(45) Date of Patent: Jun. 2, 2020

(54) COMPOSITIONS AND METHODS FOR PRODUCING STARCH WITH NOVEL FUNCTIONALITY

(71) Applicant: Corn Products Development, Inc., Westchester, IL (US)

(72) Inventors: Hongxin Jiang, Bridgewater, NJ (US); Brad Ostrander, Bridgewater, NJ (US); Chris Lane, Bridgewater, NJ (US)

(73) Assignee: Corn Products Development, Inc., Westchester, IL (US)

(*) Notice: Subject to any disclaimer, the term of this patent is extended or adjusted under 35 U.S.C. 154(b) by 160 days.

(21) Appl. No.: 15/963,885

(22) Filed: Apr. 26, 2018

(65) Prior Publication Data

US 2018/0327767 A1 Nov. 15, 2018

Related U.S. Application Data

(60) Division of application No. 15/135,106, filed on Apr. 21, 2016, now Pat. No. 9,988,641, which is a
(Continued)

(51) Int. Cl.
*C12N 15/82* (2006.01)
*A01H 5/10* (2018.01)
(Continued)

(52) U.S. Cl.
CPC ......... *C12N 15/8245* (2013.01); *A01G 22/00* (2018.02); *A01H 1/02* (2013.01);
(Continued)

(58) Field of Classification Search
None
See application file for complete search history.

(56) References Cited

U.S. PATENT DOCUMENTS 4,428,972 A 1/1984 Wurzburg et al.
4,615,888 A 10/1986 Zallie et al.
(Continued)

FOREIGN PATENT DOCUMENTS

WO 2003033540 A2 4/2003

OTHER PUBLICATIONS

Nelson, previously unreported wx heteroalleles, maize genet. coop. news letter 50, 109-113 (Year: 1976).*
(Continued)

*Primary Examiner* — Stefanie J Cohen
(74) *Attorney, Agent, or Firm* — Jacqueline Cohen; Jason Grauch; Rachael Casey

(57) ABSTRACT

This invention disclosure relates to novel maize starch. The starch can be made from the newly developed waxy sugary-2 double-mutant maize that has low activity of Granule Bound Starch Synthase I (GBSSI), which results in low amylose level. The starch from newly developed waxy sugary-2 double-mutant is freeze-thaw stable and has high viscosity. In comparison with the starch of the existing waxy sugary-2 double-mutant maize, the new waxy sugary-2 double-mutant maize starch showed, inter alia, improved pasting profile, starch granule integrity, larger starch granule size, and higher viscosity.

21 Claims, 7 Drawing Sheets

Specification includes a Sequence Listing.

Related U.S. Application Data continuation of application No. 15/090,926, filed on Apr. 5, 2016.

(51) Int. Cl.
| | | |
|---|---|---|
| *A01H 1/02* | (2006.01) | |
| *C12N 9/10* | (2006.01) | |
| *A01H 1/04* | (2006.01) | |
| *A01G 22/00* | (2018.01) | |
| *C08B 30/04* | (2006.01) | |

(52) U.S. Cl.
CPC ............... *A01H 1/04* (2013.01); *A01H 5/10* (2013.01); *C08B 30/044* (2013.01); *C12N 9/1051* (2013.01); *C12N 15/8241* (2013.01); *C12Y 204/01021* (2013.01); *C12Y 204/01242* (2013.01)

(56) References Cited

U.S. PATENT DOCUMENTS

| | | |
|---|---|---|
| 4,767,849 A | 8/1988 | Friedman et al. |
| 5,648,111 A | 7/1997 | Pearlstein et al. |
| 5,954,883 A | 9/1999 | Nagle et al. |
| 6,274,792 B1 * | 8/2001 | Chang .................. A01H 5/10 800/263 |
| 6,828,474 B2 | 12/2004 | Nagle et al. |
| 6,960,703 B2 * | 11/2005 | Nagle .................. A01H 1/02 800/263 |
| 2006/0216402 A1 | 9/2006 | Klucinec et al. |

OTHER PUBLICATIONS

Varagona et al, Alternative Splicing Induced by Insertion of Retrotransposons into the Maize waxy Gene, the plant cell, vol. 4, pp. 811-820 (Year: 1992).*

Marillonnet et al, Extreme Structural Heterogeneity Among the Members of a Maize Retrotransposon Family, genetics, 150, pp. 1245-1256 (Year: 1998).*

Wessler et al, Molecular basis of mutations at the waxy locus of maize: Correlation with the fine structure genetic map, Proc. Natl. Acad. Sci, USA, vol. 82, pp. 4177-4181, Genetics (Year: 1985).*

Varagona, Marguerite J. et al., Alternative Splicing Induced by Insertion of Retrotransposons into the Maize Waxy Gene, 1992, The Plant Cell, vol. 4, pp. 811-820.

Wessler, Susan R., et al., Molecular basis of mutations at the waxy locus of maize: Correlation with the fine structure genetic map, Proc. Nat'l. Acad. Sci., USA, 1985, vol. 82, pp. 4177-4181.

\* cited by examiner

Starch pasting profiles of waxy corn starch samples.

FIG. 2
Starch pasting properties of waxy corn starch samples.

| Sample | Pasting Temp. (°C) | Peak (RVU) | Hold (RVU) | Final (RVU) | Break Down (RVU) | Setback (RVU) |
|---|---|---|---|---|---|---|
| Q3017a (1 wxS) | 62.0 | 275.7 | 95.3 | 121.3 | 180.4 | 26.0 |
| Q8412a (2 wxS) | 59.1 | 167.8 | 102.1 | 148.0 | 65.7 | 45.9 |
| Q7738a (3 wxS) | 59.5 | 182.2 | 111.9 | 165.6 | 70.2 | 53.7 |
| wxwxwxsu2su2su2 (0 wxS) | 54.4 | 129.3 | 30.3 | 40.9 | 99.0 | 10.6 |
| K5994a (waxy Stoner) | 73.8 | 202.6 | 96.3 | 139.0 | 106.3 | 42.7 |
| AMIOCA™ starch | 72.2 | 248.2 | 96.3 | 116.8 | 151.9 | 20.5 |
| wxwxwxSU2su2su2 starch | 67.5 | 220.9 | 84.9 | 106.1 | 136.0 | 21.2 |

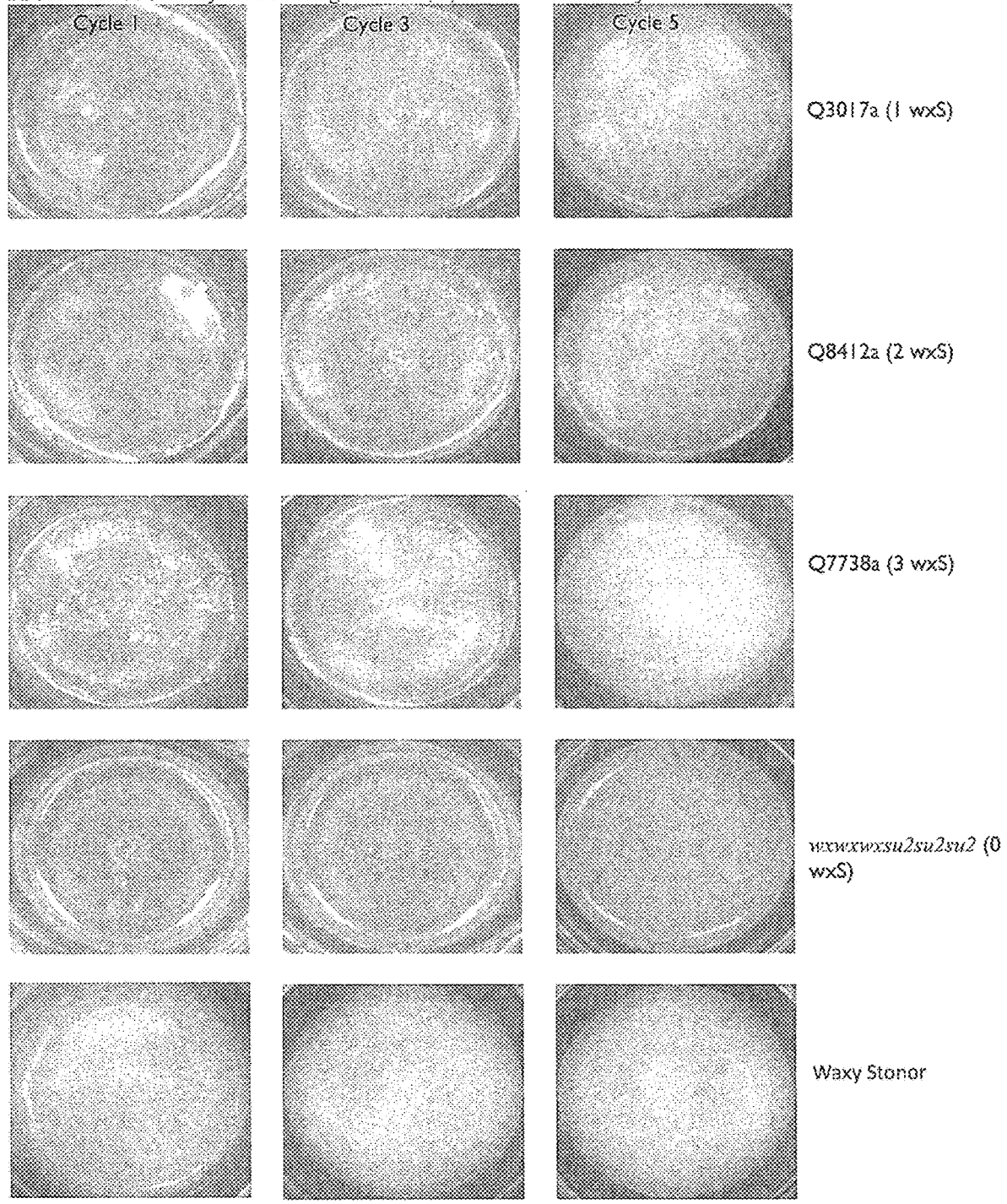
FIG. 3. Photos of waxy corn starch gels after 1, 3, and 5 freeze-thaw cycles.

*wxwxwxS U2su2su2*

AMIOCA™ starch

Cycle 1        Cycle 3        Cycle 5

FIG. 4

Thermal Properties of waxy corn starch samples.

| Sample | $T_o$ (°C) | $T_p$ (°C) | $T_c$ (°C) | ΔH (J/g) |
|---|---|---|---|---|
| Q3017a (1 wxS) | 57.2±0.0 | 62.5±0.3 | 69.3±0.2 | 12.9±0.0 |
| Q8412a (2 wxS) | 51.2±0.1 | 58.0±0.1 | 65.7±0.4 | 6.0±0.1 |
| Q7738a (3 wxS) | 51.7±0.2 | 58.2±0.4 | 66.8±0.3 | 8.0±0.1 |
| *wxwxwxsu2su2su2* | 52.2±0.2 | 58.1±0.2 | 65.6±0.0 | 4.5±0.0 |
| K5994a (Waxy Stonor) | 68.1 | 74.6 | 81.3 | 14.9 |
| AMIOCA™ starch | 66.7±0.5 | 73.5±0.3 | 80.6±0.6 | 16.6±0.2 |
| *wxwxwxSU2su2su2* starch | 60.8±0.1 | 67.8±0.1 | 77.6±0.2 | 15.4±0.0 |

Granule size distributions of waxy corn starch samples.

Granule morphology of waxy corn starch samples.

SEQUENCE LISTING

<160> NUMBER OF SEQ ID NOS: 2

<210> SEQ ID NO 1
<211> LENGTH: 605
<212> TYPE: PRT
<213> ORGANISM: Zea mays

<400> SEQUENCE: 1

```
Met Ala Ala Leu Ala Thr Ser Gln Leu Val Ala Thr Arg Ala Gly Leu
1               5                   10                  15

Gly Val Pro Asp Ala Ser Thr Phe Arg Arg Gly Ala Ala Gln Gly Leu
            20                  25                  30

Arg Gly Ala Arg Ala Ser Ala Ala Ala Asp Thr Leu Ser Met Arg Thr
        35                  40                  45

Ser Ala Arg Ala Ala Pro Arg His Gln Gln Gln Ala Arg Arg Gly Gly
    50                  55                  60

Arg Phe Pro Ser Leu Val Val Cys Ala Ser Ala Gly Met Asn Val Val
65                  70                  75                  80

Phe Val Gly Ala Glu Met Ala Pro Trp Ser Lys Thr Gly Gly Leu Gly
                85                  90                  95

Asp Val Leu Gly Gly Leu Pro Pro Ala Met Ala Ala Asn Gly His Arg
            100                 105                 110

Val Met Val Val Ser Pro Arg Tyr Asp Gln Tyr Lys Asp Ala Trp Asp
        115                 120                 125

Thr Ser Val Val Ser Glu Ile Lys Met Gly Asp Gly Tyr Glu Thr Val
    130                 135                 140

Arg Phe Phe His Cys Tyr Lys Arg Gly Val Asp Arg Val Phe Val Asp
145                 150                 155                 160

His Pro Leu Phe Leu Glu Arg Val Trp Gly Lys Thr Glu Glu Lys Ile
                165                 170                 175

Tyr Gly Pro Val Ala Gly Thr Asp Tyr Arg Asp Asn Gln Leu Arg Phe
            180                 185                 190

Ser Leu Leu Cys Gln Ala Ala Leu Glu Ala Pro Arg Ile Leu Ser Leu
        195                 200                 205

Asn Asn Asn Pro Tyr Phe Ser Gly Pro Tyr Gly Glu Asp Val Val Phe
    210                 215                 220

Val Cys Asn Asp Trp His Thr Gly Pro Leu Ser Cys Tyr Leu Lys Ser
225                 230                 235                 240

Asn Tyr Gln Ser His Gly Ile Tyr Arg Asp Ala Lys Thr Ala Phe Cys
                245                 250                 255

Ile His Asn Ile Ser Tyr Gln Gly Arg Phe Ala Phe Ser Asp Tyr Pro
            260                 265                 270

Glu Leu Asn Leu Pro Glu Arg Phe Lys Ser Ser Phe Asp Phe Ile Asp
        275                 280                 285

Gly Tyr Glu Lys Pro Val Glu Gly Arg Lys Ile Asn Trp Met Lys Ala
    290                 295                 300

Gly Ile Leu Glu Ala Asp Arg Val Leu Thr Val Ser Pro Tyr Tyr Ala
305                 310                 315                 320

Glu Glu Leu Ile Ser Gly Ile Ala Arg Gly Cys Glu Leu Asp Asn Ile
                325                 330                 335

Met Arg Leu Thr Gly Ile Thr Gly Ile Val Asn Gly Met Asp Val Ser
            340                 345                 350

Glu Trp Asp Pro Ser Arg Asp Lys Tyr Ile Ala Val Lys Tyr Asp Val
        355                 360                 365
```

```
Ser Thr Ala Val Glu Ala Lys Ala Leu Asn Lys Glu Ala Leu Gln Ala
    370                 375                 380

Glu Val Gly Leu Pro Val Asp Arg Asn Ile Pro Leu Val Ala Phe Ile
385                 390                 395                 400

Gly Arg Leu Glu Glu Gln Lys Gly Pro Asp Val Met Ala Ala Ala Ile
                405                 410                 415

Pro Gln Leu Met Glu Met Val Glu Asp Val Gln Ile Val Leu Leu Gly
                420                 425                 430

Thr Gly Lys Lys Lys Phe Glu Arg Met Leu Met Ser Ala Glu Glu Lys
            435                 440                 445

Phe Pro Gly Lys Val Arg Ala Val Val Lys Phe Asn Ala Ala Leu Ala
450                 455                 460

His His Ile Met Ala Gly Ala Asp Val Leu Ala Val Thr Ser Arg Phe
465                 470                 475                 480

Glu Pro Cys Gly Leu Ile Gln Leu Gln Gly Met Arg Tyr Gly Thr Pro
                485                 490                 495

Cys Ala Cys Ala Ser Thr Gly Gly Leu Val Asp Thr Ile Ile Glu Gly
                500                 505                 510

Lys Thr Gly Phe His Met Gly Arg Leu Ser Val Asp Cys Asn Val Val
            515                 520                 525

Glu Pro Ala Asp Val Lys Lys Val Ala Thr Thr Leu Gln Arg Ala Ile
530                 535                 540

Lys Val Val Gly Thr Pro Ala Tyr Glu Glu Met Val Arg Asn Cys Met
545                 550                 555                 560

Ile Gln Asp Leu Ser Trp Lys Gly Pro Ala Lys Asn Trp Glu Asn Val
                565                 570                 575

Leu Leu Ser Leu Gly Val Ala Gly Glu Pro Gly Val Glu Gly Glu
                580                 585                 590

Glu Ile Ala Pro Leu Ala Lys Glu Asn Val Ala Ala Pro
                595                 600                 605

<210> SEQ ID NO 2
<211> LENGTH: 729
<212> TYPE: PRT
<213> ORGANISM: Zea mays

<400> SEQUENCE: 2

Met Ser Ser Ala Ala Val Ser Ser Ser Ser Thr Phe Phe Leu Ala
1               5                   10                  15

Leu Ala Ser Ala Ser Pro Gly Gly Arg Arg Arg Ala Arg Val Gly Ser
                20                  25                  30

Ser Pro Phe His Thr Gly Ala Ser Leu Ser Phe Ala Phe Trp Ala Pro
            35                  40                  45

Pro Ser Pro Pro Arg Ala Pro Arg Asp Ala Ala Leu Val Arg Ala Glu
    50                  55                  60

Ala Glu Ala Gly Gly Lys Asp Ala Pro Pro Glu Arg Ser Gly Asp Ala
65                  70                  75                  80

Ala Arg Leu Pro Arg Ala Arg Arg Asn Ala Val Ser Lys Arg Arg Asp
                85                  90                  95

Pro Leu Gln Pro Val Gly Arg Tyr Gly Ser Ala Thr Gly Asn Thr Ala
            100                 105                 110

Arg Thr Gly Ala Ala Ser Cys Gln Asn Ala Ala Leu Ala Asp Val Glu
        115                 120                 125

Ile Lys Ser Ile Val Ala Ala Pro Pro Thr Ser Ile Val Lys Phe Pro
130                 135                 140
```

```
Ala Pro Gly Tyr Arg Met Ile Leu Pro Ser Gly Asp Ile Ala Pro Glu
145                 150                 155                 160

Thr Val Leu Pro Ala Pro Lys Pro Leu His Glu Ser Pro Ala Val Asp
            165                 170                 175

Gly Asp Ser Asn Gly Ile Ala Pro Pro Thr Val Glu Pro Leu Val Gln
            180                 185                 190

Glu Ala Thr Trp Asp Phe Lys Lys Tyr Ile Gly Phe Asp Glu Pro Asp
            195                 200                 205

Glu Ala Lys Asp Asp Ser Arg Val Gly Ala Asp Ala Gly Ser Phe
210                 215                 220

Glu His Tyr Gly Asp Asn Asp Ser Gly Pro Leu Ala Gly Glu Asn Val
225                 230                 235                 240

Met Asn Val Ile Val Val Ala Ala Glu Cys Ser Pro Trp Cys Lys Thr
                245                 250                 255

Gly Gly Leu Gly Asp Val Val Gly Ala Leu Pro Lys Ala Leu Ala Arg
            260                 265                 270

Arg Gly His Arg Val Met Val Val Pro Arg Tyr Gly Asp Tyr Val
            275                 280                 285

Glu Ala Phe Asp Met Gly Ile Arg Lys Tyr Tyr Lys Ala Ala Gly Pro
290                 295                 300

Val Asn Tyr Phe His Ala Phe Ile Asp Gly Val Asp Phe Val Phe Ile
305                 310                 315                 320

Asp Ala Pro Leu Phe Arg His Arg Gln Asp Asp Ile Tyr Gly Gly Ser
                325                 330                 335

Arg Gln Glu Ile Met Lys Arg Met Ile Leu Phe Cys Lys Val Ala Val
            340                 345                 350

Glu Val Pro Trp His Val Pro Cys Gly Gly Val Cys Tyr Gly Asp Gly
            355                 360                 365

Asn Leu Val Phe Ile Ala Asn Asp Trp His Thr Ala Leu Leu Pro Val
370                 375                 380

Tyr Leu Lys Ala Tyr Tyr Arg Asp His Gly Leu Met Gln Tyr Thr Arg
385                 390                 395                 400

Ser Val Leu Val Ile His Asn Ile Ala His Gln Gly Arg Gly Pro Val
                405                 410                 415

Asp Glu Phe Pro Tyr Met Asp Leu Pro Glu His Tyr Leu Gln His Phe
            420                 425                 430

Glu Leu Tyr Asp Pro Val Gly Gly Glu His Ala Asn Ile Phe Ala Ala
            435                 440                 445

Gly Leu Lys Met Ala Asp Arg Val Val Thr Val Ser Arg Gly Tyr Leu
            450                 455                 460

Trp Glu Leu Lys Thr Val Glu Gly Gly Trp Gly Leu His Asp Ile Ile
465                 470                 475                 480

Arg Ser Asn Asp Trp Lys Ile Asn Gly Ile Val Asn Gly Ile Asp His
            485                 490                 495

Gln Glu Trp Asn Pro Lys Val Asp Val His Leu Arg Ser Asp Gly Tyr
            500                 505                 510

Thr Asn Tyr Ser Leu Glu Thr Leu Asp Ala Gly Lys Arg Gln Cys Lys
            515                 520                 525

Ala Ala Leu Gln Arg Glu Leu Gly Leu Glu Val Arg Asp Asp Val Pro
            530                 535                 540

Leu Leu Gly Phe Ile Gly Arg Leu Asp Gly Gln Lys Gly Val Asp Ile
545                 550                 555                 560
```

```
Ile Gly Asp Ala Met Pro Trp Ile Ala Gly Gln Asp Val Gln Leu Val
            565             570             575

Met Leu Gly Thr Gly Arg Ala Asp Leu Glu Arg Met Leu Gln His Leu
            580             585             590

Glu Arg Glu His Pro Asn Lys Val Arg Gly Trp Val Gly Phe Ser Val
        595             600             605

Pro Met Ala His Arg Ile Thr Ala Gly Ala Asp Val Leu Val Met Pro
    610             615             620

Ser Arg Phe Glu Pro Cys Gly Leu Asn Gln Leu Tyr Ala Met Ala Tyr
625             630             635             640

Gly Thr Val Pro Val Val His Ala Val Gly Gly Leu Arg Asp Thr Val
            645             650             655

Ala Pro Phe Asp Pro Phe Ser Asp Ala Gly Leu Gly Trp Thr Phe Asp
            660             665             670

Arg Ala Glu Ala Asn Lys Leu Ile Glu Ala Leu Arg His Cys Leu Asp
            675             680             685

Thr Tyr Arg Asn Tyr Glu Glu Ser Trp Lys Ser Leu Gln Ala Arg Gly
    690             695             700

Met Ser Gln Asp Leu Ser Trp Asp His Ala Ala Glu Leu Tyr Glu Asp
705             710             715             720

Val Leu Val Lys Ala Lys Tyr Gln Trp
            725
```

COMPOSITIONS AND METHODS FOR PRODUCING STARCH WITH NOVEL FUNCTIONALITY

CROSS-REFERENCE TO RELATED APPLICATIONS

The present application is a Divisional of U.S. application Ser. No. 15/135,106, filed Apr. 21, 2016 and U.S. application Ser. No. 15/090,926 filed on Apr. 5, 2016, the disclosure both of which are herein incorporated by reference in their entirety for all purposes.

FIELD OF THE INVENTION

The present invention relates to maize starch derived from plants and grains, compositions and methods for producing such starch.

BACKGROUND OF THE INVENTION

The existing waxy sugary-2 double-mutant maize starch shows very good freeze/thaw stability. However, the viscosity of the existing waxy sugary-2 maize starch was substantially lower than commercial waxy maize starch, such as AMIOCA™ starch. In addition, the pasting temperature of the existing waxy sugary-2 double-mutant maize starch is substantially lower than AMIOCA™ starch. Therefore, there remains a need in the art for producing maize starch with good freeze/thaw stability, increased viscosity, and/or higher pasting temperature.

In this invention, we developed new maize starch with higher viscosity and/or higher pasting temperature than commercial waxy maize starch, such as AMIOCA™ starch, by introduction of low activity of GBSSI to the existing waxy sugary-2 double-mutant maize.

SUMMARY OF THE INVENTION

The present invention provides starch with novel functionality which has not been found in nature. In some embodiments, the starch comprises an amylose content of from about 2 wt % to about 20 wt % using an amylose/amylopectin assay kit, e.g., Megazyme®. In some embodiments, the starch comprises an aqueous starch pasting temperature that is at least about 5% greater than the starch pasting temperature of a control starch as measured using a Rapid Visco Analyzer (RVA, Newport Scientific, Sydney, Australia). In some embodiments, the starch is derived from a waxy-sugary 2 double mutant corn plant comprising at least one wx-Stonor (wxS) allele in the endosperm. In some embodiments, the waxy-sugary 2 double mutant corn plant comprises a recessive su2 mutant allele.

In some embodiments, the starch of the present invention is produced from plants which are not transgenic (i.e., non-GMO) for the genotype that produces the disclosed and claimed starch.

In some embodiments, the amylose content of the starch is from about 8 wt % to about 15 wt %.

In some embodiments, the aqueous pasting temperature is from about 5% to about 15% greater than that of a control starch.

In some embodiments, the starch further comprises an enthalpy change of crystallinity. In some embodiments, the enthalpy change of crystallinity is at least about 30% greater than an enthalpy change of crystallinity of a control starch as measured using a differential scanning calorimeter (DSC). In some embodiments, the enthalpy change of crystallinity is from about 30% to about 200% greater than an enthalpy change of crystallinity of a control starch as measured using a DSC.

In some embodiments, the starch further comprises a distribution of starch granule sizes, wherein the distribution of starch granule sizes comprises at least about 40% fewer granules less than 5 microns compared to a proportion of granules less than 5 microns from a control starch as observed using a scanning electron microscope.

In some embodiments, the starch has a granule which exhibits increased integrity compared to a starch derived from the control corn plant as observed using a scanning electron microscope.

In some embodiments, the starch is capable of withstanding at least three freeze-thaw cycles. In some embodiments, the starch is capable of withstanding at least three to at least five freeze-thaw cycles.

In some embodiments, a plant producing the starch of the present invention is generated by cross pollination of a first corn plant having the genotype of wxwxsu2su2, and a second corn plant having the genotype of wxSwxSsu2su2, or the genotype of wxSwxsu2su2. In some embodiments, the endosperm of the waxy-sugary 2 corn plant has one dose, two doses, or three doses of the wxS allele, and the endosperm has the genotype of wxSwxwxsu2su2su2, wxSwxSwxsu2su2su2, or wxSwxSwxSsu2su2su2.

The present invention also provides methods for producing the starch with an improved pasting profile. In some embodiments, the methods comprise introducing at least one wxS allele into the endosperm of a waxy corn plant.

The present invention also provides novel double-mutant plants. In some embodiments, the plants are corn plants. In some embodiments, the plants are homozygous recessive for the starch synthase IIa (su2) gene. In some embodiments, the plants are either homozygous or heterozygous for a mutated Granule-bound starch synthase I (GBSSI) gene. In some embodiments, the mutated GBSSI gene has less GBSSI activity as the wild type GBSSI gene (Wx), but has higher GBSSI activity than the recessive, loss-of-function GBSSI gene (wx).

In some embodiments, the mutated GBSSI gene has about 8% to about 10% of GBSSI activity of the wild type GBSSI gene. In some embodiments, the mutated GBSSI gene is the wx-Stonor (wxS) allele. In some embodiments, the mutated GBSSI gene is the wx-G allele, the wx-B5 allele, or the wx-M allele.

In some embodiments, the double-mutant plant is generated by cross pollination of two parent plants. In some embodiments, the first plant has the genotype of wxwxsu2su2. In some embodiments, the second plant has the genotype of wxSwxSsu2su2, or the genotype of wxSwxsu2su2.

In some embodiments, the endosperm of the plant has one dose, two doses, or three doses of the wxS allele. In some embodiments, the endosperm of the plant has the genotype of wxSwxwxsu2su2su2, wxSwxSwxsu2su2su2, or wxSwxSwxSsu2su2su2.

In some embodiments, starch produced in the endosperm of the plant has a higher viscosity compared to the starch produced in the endosperm of a double, waxy sugary-2 recessive mutant plant having the genotype of wxwxwxsu2su2su2.

In some embodiments, starch produced in the endosperm of the plant has a higher starch pasting temperature compared to the starch produced in the endosperm of a double, waxy sugary-2 recessive mutant plant having the genotype of wxwxwxsu2su2su2.

The present invention also provides plant parts, plant cells, and tissue cultures of the plants. In some embodiments, the plant part is an endosperm, a leaf, a flower, an ovule, a pollen, a rootstock, or a scion. In some embodiments, the plant part is a seed of the plants.

The present invention also provides starch extracted from plants described above.

The present invention also provides methods for producing starch. In some embodiments, the methods comprise obtaining starch from the endosperm of the plants of the present invention.

In some embodiments, the methods for producing starch comprise growing the plants of the present invention, and harvesting seeds from the plants.

The present invention also provides methods for producing a seed. In some embodiments, the methods comprise crossing a first parent plant with a second parent plant and harvesting the resultant seed. In some embodiments, said first parent plant and/or second parent plant is a plant of the present invention. In some embodiments, the methods comprise self-pollinating a plant of the present invention, and harvesting the resultant seed.

The present invention also provides methods of vegetatively propagating the plant. In some embodiments, the methods comprise collecting part of the plant and regenerating a plant from said part.

The present invention also provides methods of producing a plant derived from the plants of the present invention. In some embodiments, the methods comprise self-pollinating a plant of the present invention at least once to produce a progeny plant derived from the plant. In some embodiments, the methods comprise crossing a plant of the present invention with a second plant to produce a plant progeny.

The present invention also provides methods of producing a transgenic plant. In some embodiments, the methods comprise introducing a transgene of interest into a plant of the present invention. The transgene of interest confers one or more desired phenotypes in the plant.

The present invention also provides methods of producing a plant with desired phenotypes, comprising gene-editing to produce a genetic sequence in a plant of the present invention. The genetic sequence confers one or more desired phenotypes in the plant.

The present invention also provides methods of producing a plant with desired phenotypes, comprising inducing one or more mutations into a plant of the present invention to produce a genetic sequence. The genetic sequence confers one or more desired phenotypes in the plant.

BRIEF DESCRIPTION OF THE DRAWINGS

FIG. 2 depicts the pasting properties of AMIOCA™ starch, wxwxwxSU2su2su2 starch, and starch of waxy-sugary 2 double-mutant plants with zero, one, two, or three doses of wxS gene, including the pasting temperature, peak RVU, hold RVU, final RVU, breakdown RVU, and setback RVU.

FIG. 4 depicts the thermal properties of AMIOCA™ starch, wxwxwxSU2su2su2 starch, and starch of waxy-sugary 2 double-mutant plants with zero, one, two, or three doses of wxS gene.

DETAILED DESCRIPTION OF THE INVENTION

Definitions

Figure 1:
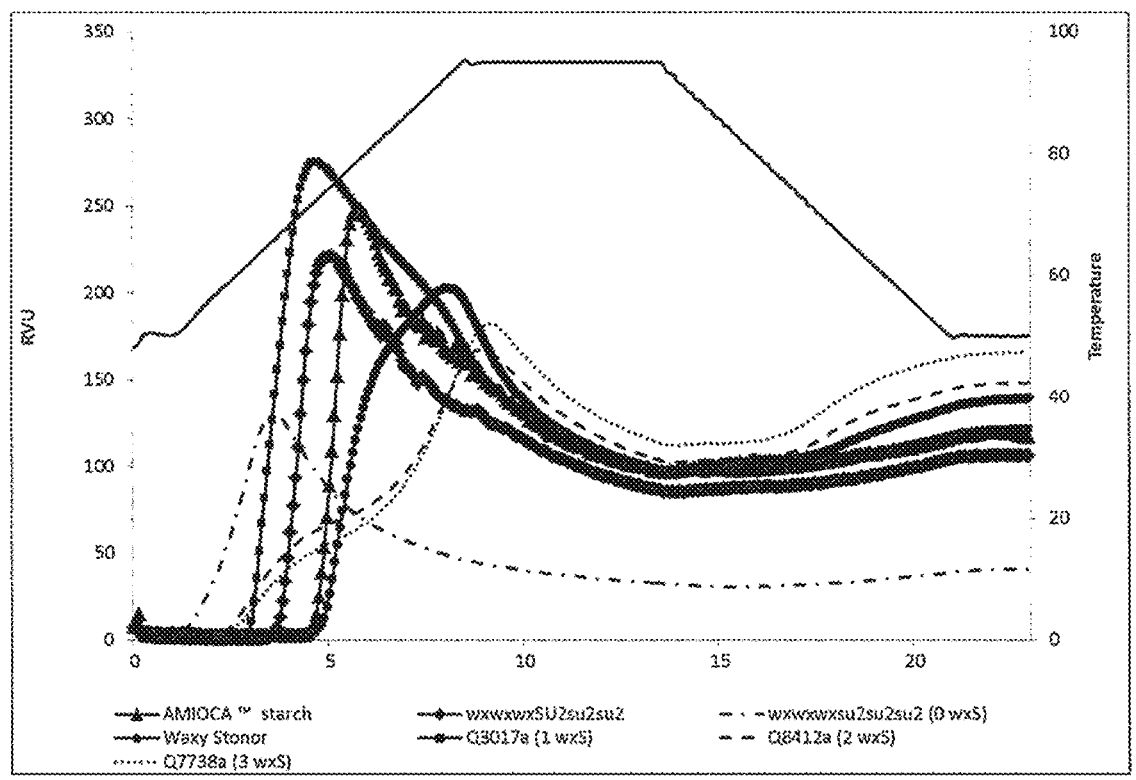
FIG. 1 depicts the pasting profiles of AMIOCA™ starch, wxwxwxSU2su2su2 starch, and starch of waxy-sugary 2 double-mutant plants with zero, one, two, or three doses of wxS gene, as measured by a Rapid Visco Analyzer (RVA) over time during the heating-cooling cycle.

As used herein, the verb "comprise" as is used in this description and in the claims and its conjugations are used in its non-limiting sense to mean that items following the word are included, but items not specifically mentioned are not excluded.

The invention provides compositions and methods to produce plants. As used herein, the term "plant" refers to any living organism Plantae (i.e., any genus/species in the Plant Kingdom). In some embodiments, the plant is capable of producing starch, including but not limited to maize, potato, wheat, tapioca, rice, potato and sorghum. In some embodiments, the plant is a corn plant.

The invention provides plant parts. As used herein, the term "plant part" refers to any part of a plant including but not limited to the embryo, endosperm, shoot, root, stem, seed, stipule, leaf, petal, flower, ovule, bract, branch, petiole, internode, bark, pubescence, tiller, rhizome, frond, blade, ovule, pollen, stamen, and the like.

The invention provides genes comprising the isolated (e.g., wild type, endogenous to the organism), chimeric, recombinant or synthetic nucleic acid sequence. As used herein, the term "gene" refers to any segment of DNA associated with a biological function. Thus, genes include, but are not limited to, coding sequences and/or the regulatory sequences required for their expression. Genes can also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

The invention provides polynucleotides with nucleotide change when compared to a wild type reference sequence. As used herein, the term "nucleotide change" refers to, e.g., nucleotide substitution, deletion, insertion, or transposon, as is well understood in the art. For example, mutations contain alterations that produce silent substitutions, additions, deletions, or alternative splicing, which either alter or do not alter the properties or activities of the encoded protein or how the proteins are made. A nucleotide change can also be insertion and/or exclusion of a retrotransposon element in the gene.

The invention provides polypeptides with protein modification when compared to a wild-type reference sequence. As used herein, the term "protein modification" refers to, e.g., amino acid substitution, amino acid modification, deletion, insertion, or change of protein activity, as is well understood in the art.

The invention provides polynucleotides and polypeptides derived from wild-type reference sequences. As used herein, the term "derived from" refers to the origin or source, and may include naturally occurring, recombinant, unpurified, or purified molecules. A nucleic acid or an amino acid derived from an origin or source may have all kinds of nucleotide changes or protein modification as defined elsewhere herein.

The invention provides biologically active variants or functional variants of the nucleic acid sequences and polypeptide sequences of the present invention. As used herein, the phrase "a biologically active variant" or "functional variant" with respect to a protein refers to an amino acid sequence that is altered by one or more amino acids with respect to a reference sequence, while still maintains substantial biological activity of the reference sequence. The variant can have "conservative" changes, wherein a substituted amino acid has similar structural or chemical properties, e.g., replacement of leucine with isoleucine. The following table shows exemplary conservative amino acid substitutions. In some embodiments, the variant has one or more amino acid substitutions, wherein one or more or all substitutions are acidic amino acid, such as Aspartic acid, Asparagine, Glutamic acid, or Glutamine.

polynucleotide. As used herein, a "reference" polynucleotide comprises a nucleotide sequence produced by the methods disclosed herein. Variant polynucleotides also include synthetically derived polynucleotides, such as those generated, for example, by using site directed mutagenesis but which still comprise genetic regulatory element activity. Generally, variants of a particular polynucleotide or nucleic acid molecule, or polypeptide of the invention will have at least about 60%, 65%, 70%, 75%, 80%, 85%, 90%, 91%, 91.5%, 92%, 92.5%, 93%, 93.5%, 94%, 94.5%, 95%, 95.5%, 96%, 96.5%, 97%, 97.5%, 98%, 98.5%, 99%, 99.1%, 99.2%, 99.3%, 99.4%, 99.5%, 99.6%, 99.7%, 99.8%, 99.9% or more sequence identity to that particular polynucleotide/polypeptides as determined by sequence alignment programs and parameters as described elsewhere herein.

Variant polynucleotides also encompass sequences derived from a mutagenic and recombinogenic procedure such as DNA shuffling. Strategies for such DNA shuffling are known in the art. See, for example, Stemmer (1994) *PNAS* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *PNAS* 94:4504-4509; Crameri et al. (1998) *Nature* 391:288-291; and U.S. Pat. Nos. 5,605,793 and 5,837,458. For PCR amplifications of the polynucleotides disclosed herein, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory*

| Original Residue | Very Highly - Conserved Substitutions | Highly Conserved Substitutions (from the Blosum90 Matrix) | Conserved Substitutions (from the Blosum65 Matrix) |
| --- | --- | --- | --- |
| Ala | Ser | Gly, Ser, Thr | Cys, Gly, Ser, Thr, Val |
| Arg | Lys | Gln, His, Lys | Asn, Gln, Glu, His, Lys |
| Asn | Gln; His | Asp, Gln, His, Lys, Ser, Thr | Arg, Asp, Gln, Glu, His, Lys, Ser, Thr |
| Asp | Glu | Asn, Glu | Asn, Gln, Glu, Ser |
| Cys | Ser | None | Ala |
| Gln | Asn | Arg, Asn, Glu, His, Lys, Met | Arg, Asn, Asp, Glu, His, Lys, Met, Ser |
| Glu | Asp | Asp, Gln, Lys | Arg, Asn, Asp, Gln, His, Lys, Ser |
| Gly | Pro | Ala | Ala, Ser |
| His | Asn; Gln | Arg, Asn, Gln, Tyr | Arg, Asn, Gln, Glu, Tyr |
| Ile | Leu; Val | Leu, Met, Val | Leu, Met, Phe, Val |
| Leu | Ile; Val | Ile, Met, Phe, Val | Ile, Met, Phe, Val |
| Lys | Arg; Gln; Glu | Arg, Asn, Gln, Glu | Arg, Asn, Gln, Glu, Ser, |
| Met | Leu; Ile | Gln, Ile, Leu, Val | Gln, Ile, Leu, Phe, Val |
| Phe | Met; Leu; Tyr | Leu, Trp, Tyr | Ile, Leu, Met, Trp, Tyr |
| Ser | Thr | Ala, Asn, Thr | Ala, Asn, Asp, Gln, Glu, Gly, Lys, Thr |
| Thr | Ser | Ala, Asn, Ser | Ala, Asn, Ser, Val |
| Trp | Tyr | Phe, Tyr | Phe, Tyr |
| Tyr | Trp; Phe | His, Phe, Trp | His, Phe, Trp |
| Val | Ile; Leu | Ile, Leu, Met | Ala, Ile, Leu, Met, Thr |

Alternatively, a variant can have "nonconservative" changes, e.g., replacement of a glycine with a tryptophan. Analogous minor variations can also include amino acid deletion or insertion, or both. Guidance in determining which amino acid residues can be substituted, inserted, or deleted without eliminating biological or immunological activity can be found using computer programs well known in the art, for example, DNASTAR software. For polynucleotides, a variant comprises a polynucleotide having deletions (i.e., truncations) at the 5' and/or 3' end; deletion and/or addition of one or more nucleotides at one or more internal sites in the reference polynucleotide; and/or substitution of one or more nucleotides at one or more sites in the reference

*Manual* (2nd ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

The invention provides transgenic plants. As used herein, the term "transgenic" refers to cells, cell cultures, organisms (e.g., plants), and progeny which have received a foreign or modified gene by one of the various methods of transformation, wherein the foreign or modified gene is from the same or different species than the species of the organism receiving the foreign or modified gene.

Waxy gene: Waxy gene is the granule-bound starch synthase I (GBSSI) gene. The gene encodes a starch granule-bound ADP-glucose-glucosyl transferase (EC 2.4.1.242) responsible for amylose biosynthesis in the triploid endosperm of the developing kernel and in haploid pollen and embryo sac. "Wx" refers to the wild type allele, and "wx" refers to the null, reference mutant-allele. The terms wxS (a.k.a. wx-Stonor), wx-G, wx-B5, and wx-M refer to the intermediate alleles having retrotransposon insertion in the waxy gene, as described in Wessler and Varagona (PNAS, 82:4177-4181, 1985) and Varagona et al. (The Plant Cell, 4:811-820, 1992), each of which is herein incorporated by reference in its entirety. These intermediate alleles result in less waxy protein activity in plants having the alleles than the waxy protein activity in wild type plants. The maize waxy gene encodes the protein having the sequence of SEQ ID NO: 1.

wx-Stonor: The wx-Stonor allele in maize plant is caused by a retrotransposon insertion at the splice donor site of intron 5 of the waxy gene. Although the insertion does not affect the splicing machinery, it leads to a lower level of enzymatic activity compared to the wild type allele (e.g., only about 9.5% GBSSI activity as of the wild type). As a result, plants having wx-Stonor allele has higher amylose level than the same plant which does not have the wx-Stonor allele.

Sugary-2 gene: Sugary-2 gene encodes starch synthase isoform IIa (SSIIa, EC 2.4.1.21). "SU2" refers to the wild type allele, and "su2" refers to the recessive, mutant allele. The function of Sugary-2 protein in maize is described in Zhang et al. (Plant Molecular Biology, 54(6):865-879, 2004), which is herein incorporated by reference in its entirety. The maize wild type SU2 gene encodes the wild type protein having the sequence of SEQ ID NO: 2.

More detail of the waxy gene and the sugary-2 gene in maize are described in U.S. Pat. Nos. 4,428,972, 5,954,883, 6,828,474, 6,960,703, and 7,678,898, each of which is herein incorporated by reference in its entirety.

AMIOCA™ starch: the term refers to the AMIOCA™ corn starch produced by National Starch and Chemical Company, now Ingredion Incorporated.

wxwxwxSU2su2su2 starch: the term refers to starch isolated from maize endosperm having the genotype of wxwxwxSU2su2su2.

wxwxwxsu2su2su2 starch: the term refers to starch isolated from maize endosperm having the genotype of wxwxwxsu2su2su2, which is the endosperm of the waxy sugary-2 double recessive mutant. The mutated waxy gene contributes to its good freeze-thaw stability, and the mutated sugary-2 gene results in short branch-chain length. However, the starch has low integrity of starch granules. The granules break down easily, and the starch has low viscosity.

MELOJEL® starch: the term refers to the MELOJEL® corn starch produced by National Starch and Chemical Company, now Ingredion Incorporated.

Control corn plant: the term refers to a proper check plant for comparison. In some embodiments, a check plant can be a wild type plant. In some embodiments, the check plant is a plant that does not have an intermediate waxy gene as described herein. In some embodiments, the check plant is a corn plant that produces a wxwxwxSU2su2su2 starch or a wxwxwxsu2su2su2 starch. Accordingly, in some embodiments, the control corn plant is a corn plant which does not possess a wx-S allele in the endosperm.

Control starch: the terms refers to a control starch.

wxSwxwxsu2su2su2: the term refers to a maize endosperm with one dose of wxS.

wxSwxwxsu2su2su2 starch: the term refers to a starch isolated from maize endosperm with one dose of wxS, the endosperm having the genotype wxSwxwxsu2su2 su2.

wxSwxSwxsu2su2su2: the term refers to a maize endosperm with two doses of wxS.

wxSwxSwxsu2su2su2 starch: the term refers to a starch isolated from maize endosperm with two doses of wxS, the endosperm having the genotype wxSwxSwxsu2su2su2.

wxSwxSwxSsu2su2su2: the term refers to a maize endosperm with three doses of wxS.

wxSwxSwxSsu2su2su2 starch: the term refers to a starch isolated from maize endosperm with three doses of wxS, the endosperm having the genotype wxSwxSwxSsu2su2su2.

The following examples illustrate various aspects of the invention. The examples should, of course, be understood to be merely illustrative of only certain embodiments of the invention and not to constitute limitations upon the scope of the invention.

Starch with Novel Functionalities

In one aspect, the disclosure provides for a starch derived from a double-mutant corn plant comprising an intermediate GBSSI allele which has less GBSSI activity than a wild type GBSSI gene (Wx), but has higher GBSSI activity than a recessive, loss-of-function GBSSI gene (wx). In some embodiments, the double-mutant corn plant with an intermediate GBSSI allele is a waxy-sugary 2 corn plant comprising at least one wx-Stonor (wxS) allele in the endosperm. In some embodiments, the waxy-sugary 2 corn plant is generated by cross pollination of a first corn plant having the genotype of wxwxsu2su2, and a second corn plant having the genotype of wxSwxSsu2su2 or the genotype of wxSwxsu2su2. In further embodiments, the endosperm of the waxy-sugary 2 corn plant has one dose, two doses, or three doses of the wxS allele, and the endosperm has the genotype of wxSwxwxsu2su2su2, wxSwxSwxsu2su2su2, or wxSwxSwxSsu2su2su2.

In some embodiments, the starch comprises an amylose content of from about 2 wt % to about 20 wt % as measured using a Megazyme® amylose/amylopectin assay kit, and an aqueous starch pasting temperature that is at least about 5% greater than the pasting temperature of a control starch as measured using RVA analysis.

Amylose Content.

Starch is comprised of amylose and amylopectin. Amylose is a helical polymer made of α-D-glucose units, connected through α(1→4) glycosidic bonds. Amylopectin is a highly branched polymer of glucose comprising α(1→4) and α(1→6) glycosidic bonds. Branching takes place with the α(1→6) bonds, which occurs at approximately every 24 to 30 glucose units. In some embodiments, the amylose content in starch can be measured using an amylose/amylopectin assay kit, such as the amylose/amylopectin assay kit manufactured by Megazyme®, as set forth in the Examples section.

An intermediate mutation of the GBSSI gene in the double-mutant corn plant was observed to increase amylose content in the starch derived therefrom relative to a control corn plant with the null-allele GBSSI gene. For example, amylose content of a starch derived from a waxy-sugary 2 corn plant comprising at least one wx-Stonor (wxS) allele in the endosperm was observed to increase relative to a control corn plant. In some embodiments, the starch derived from a corn plant with at least one wx-Stonor (wxS) allele in the endosperm has an amylose content of from about 2 wt % to about 20 wt %, from about 4 wt % to about 18 wt %, from about 5 wt % to about 15 wt %, or about 8 wt % to about 15 wt %, including all values and subranges in between. In other embodiments, the amylose content is about 5 wt %, about 6 wt %, about 7 wt %, about 8 wt %, about 9 wt %, about 10 wt %, about 11 wt %, about 12 wt %, about 13 wt %, about 14 wt %, about 15 wt %, about 16 wt %, about 17 wt %, or about 18 wt %, including all values between.

Without being limited by theory, an increase in the amylose content would be expected to decrease the amylopectin content in the starch, thereby decreasing the total number glucose units and hydrogen-bonding groups available to interact with an aqueous medium. Such a decrease in hydrogen bonding should correspond to an overall decrease in the strength of the interaction of said starch with the aqueous medium and diminish the pasting properties of the starch. However, an unexpected improvement in the pasting profile was observed when the amylose content was increased in the starch disclosed herein. Without being limited by theory, this unexpected result can be attributed to an increase in the branch-chain length observed in a waxy-sugary 2 corn plant comprising at least one wx-Stonor (wxS) allele in the endosperm. Longer branch chains on the starch present more glucose units, which increase the number of hydrogen bonding interactions with the aqueous medium compared to shorter branch chain lengths.

The pasting profile of a starch can be measured by known methods, such as using a Rapid Visco Analyzer (RVA) (Newport Scientific, Sydney, Australia). For example, RVA can measure pasting temperature (° C.), peak viscosity (RVU), hold viscosity (RVU), final viscosity (RVU), breakdown viscosity (RVU), and set back viscosity (RVU). In some embodiments, the improved pasting profile allows gelatinization to occur, inter alia, at a lower effective amount of the starch and/or at a higher pasting temperature compared to a control starch. Starch gelatinization refers to a process of breaking intermolecular bonds of starch molecules in the presence of water and heat, allowing the hydrogen bonding sites (e.g., hydroxyl groups) to bind more water. To measure a starch pasting profile, an effective amount of a starch can be added to an aqueous solution at neutral pH. For example, starch can be added to an aqueous solution at 8 w/w % solids level.

Pasting Temperature.

Pasting temperature, as used herein, is intended to be measured as set forth in the Examples section. The pasting temperature of starch is the temperature at which initial swelling of starch granules takes place when suspended in water. In some embodiments, the starch described herein has an aqueous pasting temperature that is at least about 5% greater than the pasting temperature of a control starch as measured using RVA analysis. In some embodiments, the aqueous pasting temperature is increased by about 1% to about 100%, about 1% to about 50%, about 5% to about 50%, about 5% to 40%, about 5% to about 30%, about 5% to about 25%, about 5% to about 20% or about 5% to about 14%, including all values and subranges in between. In a particular embodiment, the aqueous pasting temperature is from about 5% to about 14% greater than that of a control corn plant, such as a double mutant waxy-sugary 2 corn plant.

In other embodiments, the aqueous pasting temperature is increased by at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 15%, at least about 16%, at least about 17%, at least about 18%, at least about 19%, or at least about 20% greater compared to a pasting temperature of a control starch, including all values in between.

In still other embodiments, the aqueous pasting temperature is increased by 1° C. to about 20° C., or about 5° C. to about 10° C., including all values and subranges in between. In other embodiments, the aqueous pasting temperature is increased at least about 4° C., at least about 5° C., at least about 6° C., at least about 7° C., at least about 8° C., at least about 9° C., at least about 10° C., at least about 11° C., at least about 12° C., at least about 13° C., at least about 14° C., or at or about 15° C. compared to a pasting temperature of a control starch.

In still other embodiments, the starch described herein has an aqueous pasting temperature of at least about 50° C., at least about 55° C., at least about 60° C., at least about 65° C., at least about 70° C., at least about 75° C., at least about 80° C., at least about 85° C., at least about 90° C., at least about 95° C., or at least about 100° C. In particular embodiments, the starch derived from a waxy-sugary 2 corn plant comprising at least one wx-Stonor (wxS) allele in the endosperm has an aqueous pasting temperature of from about 55° C. to about 68° C., or from about 59° C. to about 65° C., including all values and subranges in between. In yet other embodiments, the aqueous pasting temperature is about 59° C., about 60° C., about 61° C., about 62° C., about 63° C., about 64° C., about 65° C., about 66° C., about 67° C., or about 68° C., including all values in between.

Enthalpy Change of Crystallinity.

Enthalpy change of crystallinity, as used herein, is intended to be measured as set forth in the Examples section. Crystallization refers to the process of forming solid crystals from a solution by precipitation. In some embodiments, introduction of at least one wx-Stonor (wxS) allele in the endosperm of a in a waxy-sugary 2 double-mutant corn plant was observed to increase the enthalpy change of crystallinity relative to a starch from a control corn plant. Enthalpy change can be measured using, e.g., differential scanning calorimetry (DSC). In some embodiments, the enthalpy change of crystallinity is increased by about 10% to about 300%, about 10% to about 200%, about 10% to about 150%, about 10% to about 100%, or about 10% to about 50%, including all values and subranges in between. In one such embodiment, the enthalpy change of crystallinity is from about 70% to about 200% greater than an enthalpy change of crystallinity of a control starch as measured using a DSC.

In some embodiments, the enthalpy change of crystallinity is increased by at least about 10%, at least about 20%, at least about 30%, at least about 40%, at least about 50%, at least about 60%, at least about 70%, at least about 80%, at least about 90%, at least about 100%, at least about 110%, at least about 120%, at least about 130%, at least about 140%, at least about 150%, at least about 160%, at least about 170%, at least about 180%, at least about 190%, or at least about 200%, including all values in between.

In some embodiments, the enthalpy change of crystallinity is from about 1 J/g to about 20 J/g, about 5 J/g to about 15 J/g, about 6 J/g to about 13 J/g, including all values and subranges in between. In other embodiments, the enthalpy change of crystallinity 8 w/w % is about 4 J/g, about 5 J/g, about 6 J/g, about 7 J/g, about 8 J/g, about 9 J/g, about 10 J/g, about 11 J/g, about 12 J/g, about 13 J/g, including all values in between. In a particular embodiment, the corn plant comprises one wxS allele in the endosperm, and the enthalpy change of crystallinity is at least about 150% greater than that of a starch derived from a control plant with the endosperm genotype of wxwxwxsu2su2su2. In another particular embodiment, the corn plant comprises two wxS alleles in the endosperm, and the enthalpy change of crystallinity is at least about 30% greater than that of a starch derived from a control plant with the endosperm genotype of wxwxwxsu2su2su2. In yet another particular embodiment, the corn plant comprises three wxS alleles in the endosperm, and the enthalpy change of crystallinity is at least about 75% greater than that of a starch derived from a control plant with the endosperm genotype of wxwxwxsu2su2su2.

Freeze Thaw Stability.

Freeze thaw stability, as used herein, is intended to be measured as set forth in the Examples section. In some embodiments, the starch described herein exhibits desirable freeze-thaw characteristics, e.g., improved freeze-thaw stability. Freeze-thaw stability can be measured by adding an effective amount of a starch to water to form a slurry, which is then cooked and syneresis is measured after cycles of freezing/cooling. In some embodiments, introduction of at least one wx-Stonor (wxS) allele into the endosperm of a corn plant did not reduce the freeze-thaw stability of the starch derived therefrom compared to a control starch. In other embodiments, introduction of at least one wx-Stonor (wxS) allele into the endosperm of a corn plant improved the freeze-thaw stability of the starch. In one such embodiment, the starch is capable withstanding a total of at least three to at least five freeze-thaw cycles.

Granule Distribution and Integrity.

Granule distribution and integrity, as used herein, is intended to be measured as set forth in the Examples section.

In some embodiments, introduction of at least one wx-Stonor (wxS) allele in the endosperm of a corn plant was observed to alter the distribution of sizes of starch granules relative to a control starch. In some such embodiments, the distribution of starch granule sizes of a starch described herein comprises at least about 40% fewer granules less than 5 microns compared to a proportion of granules less than 5 microns from a control starch as observed using a scanning electron microscope.

Granule integrity, as used herein, refers to the ability of the starch to remain as an intact granule after dissolution in an aqueous medium. In some embodiments, the starch described herein is a granule which exhibits increased integrity compared to a starch derived from the control corn plant as observed using a scanning electron microscope.

Viscosity.

Viscosity, as used herein, is intended to be measured as set forth in the Examples section. In some embodiments, the starch described herein has an aqueous peak viscosity that is at least about 10% greater than the aqueous peak viscosity of a control starch as measured using RVA analysis. In some embodiments, the aqueous peak viscosity was increased by about 10% to about 300%, about 10% to about 250%, about 10% to about 200%, about 10% to about 150%, about 10% to about 100%, or about 10% to about 50%, including all values and subranges in between. In some embodiments, the aqueous peak viscosity was increased by at least about 10%, at least about 20%, at least about 30%, at least about 40%, at least about 50%, at least about 60% at least about 70%, at least about 80%, at least about 90%, at least about 100%, at least about 110%, at least about 120%, at least about 130%, at least about 140%, at least about 150%, at least about 160%, at least about 170%, at least about 180%, at least about 190%, or at least about 200%, including all values in between.

In some embodiments, the aqueous peak viscosity of the starch at 8 w/w % solids is about 100 RVU to about 500 RVU, about 100 RVU to about 400 RVU, about 100 RVU to about 300 RVU, about 100 RVU to about 200 RVU, or about 100 RVU to about 150 RVU, including all values and subranges in between. Is some embodiments, the aqueous peak viscosity is about 150 RVU, about 155 RVU, about 160 RVU, about 165 RVU, about 170 RVU, about 175 RVU, about 180 RVU, about 185 RVU, about 190 RVU, about 195 RVU, about 200 RVU, about 205 RVU, about 210 RVU, about 215 RVU, about 220 RVU, about 225 RVU, about 230 RVU, about 235 RVU, about 240 RVU, about 245 RVU, about 250 RVU, about 255 RVU, about 260 RVU, about 265 RVU, about 270 RVU, about 275 RVU, about 280 RVU, about 285 RVU, about 290 RVU, about 295 RVU, about 300 RVU, about 305 RVU, about 310 RVU, about 315 RVU, about 320 RVU, about 325 RVU, about 330 RVU, about 335 RVU, about 340 RVU, about 345 RVU, about 350 RVU, about 355 RVU, about 360 RVU, about 365 RVU, about 370 RVU, about 375 RVU, about 380 RVU, about 385 RVU, about 390 RVU, about 395 RVU, or about 400 RVU, including all values in between.

In a particular embodiment, the waxy-sugary 2 corn plant comprises one wx-Stonor (wxS) allele in the endosperm, and the starch has a peak viscosity of about 110% greater than that of a control plant with the endosperm genotype of wxwxwxsu2su2su2. In another particular embodiment, the waxy-sugary 2 corn plant comprises two wx-Stonor (wxS) alleles in the endosperm, and the starch has a peak viscosity of about 30% greater than that of a control plant with the endosperm genotype of wxwxwxsu2su2su2. In yet another particular embodiment, the waxy-sugary 2 corn plant comprises three wx-Stonor (wxS) alleles in the endosperm, and the starch has a peak viscosity of about 40% greater than that of a control plant with the endosperm genotype of wxwxwxsu2su2su2. In even another particular embodiment, the waxy-sugary 2 corn plant comprises two wx-Stonor (wxS) alleles in the endosperm, and the starch has a peak viscosity of about 20% greater than that of a control plant with the endosperm genotype of wxwxwxSU2su2su2. In still another particular embodiment, the waxy-sugary 2 corn plant comprises two wx-Stonor (wxS) alleles in the endosperm, and the starch has a peak viscosity is at least about 30% greater than that of a control plant with the endosperm genotype of wxwxwxSU2su2su2.

Extraction.

Extraction of the starch from the kernel of the plants of the present invention may be carried out in a standard manner by the wet-milling or dry-milling process well known in the art, but is not limited to such methods. In one typical wet-milling process, the plant is cleaned by strong currents of air, sifters and electromagnets to remove unwanted material. It is thereafter steeped in warm water containing a small amount of sulfur dioxide. The steep-water is drawn off and the softened kernels are run through attrition mills to tear them apart. The germ is removed and the remaining mixture is ground, washed and sieved as a slurry. The starch is separated from the gluten by centrifugation, and the remaining slurried starch is then filtered, washed, resuspended and refiltered.

Extraction of flour or variants thereof from the plant can be accomplished by a dry-milling process. In a typical procedure which is suitable herein but not exclusive of other procedures, the grain obtained from a plant of the present invention is first thoroughly cleaned and passed through a scourer and is then tempered or conditioned and passed through a degerminator. Stock from the degerminator is dried and then cooled, passed through a hominy separator and aspirator, ground, and finally sifted according to whether whole or separate fractions are desired.

Modification.

It can be understood that some modifications in either of the above extraction processes such, for example, as using a steep-water temperature below that which is commonly employed, may be desirable and will be easily recognized by a starch practitioner.

The starch herein may be modified, if desired, by procedures known in the art, such as by derivatization to form ethers or esters such as hydroxypropyl ethers, acetates, phosphates, succinates, e.g., octenyl succinate, tertiary and quaternary amine ethers, etc., or by any other modification techniques which produce a starch having the characteristics defined herein. The preferred substituent groups herein are hydroxypropyl, phosphate or acetate groups.

For commercial purposes, one modification of the starch herein is crosslinking to strengthen the granules against the handling and processing conditions frequently encountered in manufacturing operations and to provide a starch capable of imparting desirable rheological properties to food systems. Any cross-linking agent known in the art may be employed for this purpose, including but not limited to epichlorohydrin, linear dicarboxylic acid anhydrides, citric acid acrolein, phosphorus oxychloride, adipic/acetic mixed acid anhydrides, and trimetaphosphate salts for food systems and to epichlorohydrin, linear dicarboxylic acid anhydrides, citric acid acrolein, phosphorus oxychloride, adipic/acetic mixed acid anhydrides, trimetaphosphate salts, formaldehyde, cyanuric chloride, diioscyanates, and divinyl sulfones in non-food systems. The cross-linking reaction is carried out using techniques known in the art, for example those described in U.S. Pat. Nos. 2,328,537 and 2,801,242. Procedures for modifying starches are described in the Chapter "Starch and Its Modification" by M. W. Rutenberg, pages 22-26 to 22-47, Handbook of Water Soluble Gums and Resins, R. L. Davidson, Editor (McGraw-Hill, Inc., New York, N.Y. 1980).

The amount of crosslinking agent necessary to give a suitable product will vary depending, for example, on the type of crosslinking agent employed, the concentration of the crosslinking agent, the reaction conditions, and the necessity for having a crosslinked starch which falls within the desired viscosity range. The practitioner will recognize which amounts may be employed, as these are well known in the art. Typically, this amount will range from as low as about 0.001%, by weight of the starch, to as high as is considered acceptable for food use.

The present starches may also be physically modified, such as by thermal inhibition described in WO 95/04082 (published Feb. 9, 1995).

Processing.

The starches may also be pregelatinized. Exemplary processes for preparing pregelatinized starches are disclosed in U.S. Pat. No. 4,280,851 (Pitchon, et al.), U.S. Pat. No. 4,465,702 (Eastman, et al.), U.S. Pat. No. 5,037,929 (Rajagopalan), U.S. Pat. No. 5,131,953 (Kasica, et al.), and U.S. Pat. No. 5,149,799 (Rubens). Conventional procedures for pregelatinizing starch are well known to those skilled in the art and described in such articles as Chapter XXII—"Production and Use of Pregelatinized Starch", Starch: Chemistry and Technology, Vol. III—Industrial Aspects, R. L. Whistler and E. F. Paschall, Editors, Academic Press, New York 1967.

The present starches may be purified by any method known in the art to remove off-flavors and colors that are native to the starch or created during starch modification processes. Purification processes preferred for treating the present starches are disclosed in U.S. Ser. No. 07/832,838 filed Feb. 7, 1992, by Kasica, et al. Alkali washing techniques, for starches intended for use in either granular or pregelatinized form, are also useful and described in the family of patents represented by U.S. Pat. No. 5,187,272 (Bertalan, et al.).

Conversion products derived from the present starches, including but not limited to fluidity or thin-boiling starches prepared by oxidation, enzyme conversion particularly by α-amylase, acid hydrolysis, heat and or acid dextrinization, thermal and or sheared products are also useful herein.

Plants Producing Starch

The present invention provides plants producing starch described above. The starch producing plants include, but are not limited to maize, potato, wheat, tapioca, rice, cassava, and sorghum.

The starch of the present invention can be extracted from corn plants, such as from the endosperm of corn plants. The corn plants that produce starch of the present invention are double mutant plants of the waxy/sugary-2 genotype. The waxy gene is located at Chromosome 9 of corn while the sugary-2 gene is located at Chromosome 6. (See M. G. Nueffer, L. Jones, and M. Zuber, "The Mutants of Maize" (Crop Science Society of America, Madison, Wis., 1968), pp. 72 and 73.).

The plants of the present invention are homozygous recessive for the starch synthase IIa (su2) gene, and either homozygous or heterozygous for a mutated granule-bound starch synthase I (GBSSI) gene. The mutated GBSSI gene has less GBSSI activity than the wild type GBSSI gene (Wx), but has higher GBSSI activity than the recessive, loss-of-function GBSSI gene (wx). As used herein, such a waxy mutant gene is called an intermediate waxy mutant. In some embodiments, the intermediate waxy mutant has less than 30%, less than 25%, less than 20%, less than 15%, less than 10%, or less than 5% of the wild type GBSSI gene expression. In some embodiments, the intermediate waxy mutant has about 5%, about 6%, about 7%, about 8%, about 9%, about 10%, about 11%, about 12%, about 13%, about 14%, or about 15% of the wild type GBSSI gene expression.

An intermediate GBSSI gene having less GBSSI activity than the wild type GBSSI gene but higher GBSSI activity than the recessive, loss-of-function GBSSI gene can be either those previously known in the field, or be created by any suitable mutagenesis method.

Mutant alleles such as wxS (a.k.a. wx-Stonor), wx-G, wx-B5, and wx-M have intermediate GBSSI activity. These mutant alleles are due to retrotransposon insertion in the GBSSI gene, as described in Wessler and Varagona (PNAS, 82:4177-4181, 1985) and Varagona et al. (The Plant Cell, 4:811-820, 1992). These intermediate alleles result in a waxy protein having less activity than the wild type waxy protein.

Additional mutant alleles having intermediate GBSSI activity can be created by suitable methods. For example, retrotransposon mutagenesis can be used to generate a population for screening corn plants having a mutated GBSSI gene that has intermediate GBSSI activity. In some embodiments, wxS (a.k.a. wx-Stonor), wx-G, wx-B5, and wx-M can be used as starting materials to produce additional mutant alleles.

Other mutagenesis methods that can be used to produce mutant alleles having intermediate GBSSI activity include, but are not limited to, chemical mutagenesis, radiation mutagenesis, transposon mutagenesis, insertional mutagenesis, signature tagged mutagenesis, site-directed mutagenesis, and natural mutagenesis.

Still in some embodiments, antisense RNA, ribozyme, dsRNAi, RNA interference (RNAi) can be used to produce mutant alleles having intermediate GBSSI activity. Antisense RNA technology involves expressing in, or introducing into, a cell an RNA molecule (or RNA derivative) that is complementary to, or antisense to, sequences found in a particular mRNA in a cell. By associating with the mRNA, the antisense RNA can inhibit translation of the encoded gene product. The use of antisense technology to reduce or inhibit the expression of specific plant genes has been described, for example in European Patent Publication No. 271988, Smith et al., Nature, 334:724-726 (1988); Smith et. al., Plant Mol. Biol., 14:369-379 (1990)). A ribozyme is an RNA that has both a catalytic domain and a sequence that is complementary to a particular mRNA. The ribozyme functions by associating with the mRNA (through the complementary domain of the ribozyme) and then cleaving (degrading) the message using the catalytic domain. RNA interference (RNAi) is the process of sequence-specific, post-transcriptional gene silencing or transcriptional gene silencing in animals and plants, initiated by double-stranded RNA (dsRNA) that is homologous in sequence to the silenced gene. The RNAi technique is discussed, for example, in Elibashir, et al., Methods Enzymol. 26:199 (2002); McManus & Sharp, Nature Rev. Genetics 3:737 (2002); PCT application WO 01/75164; Martinez et al., Cell 110:563 (2002); Elbashir et al., supra; Lagos-Quintana et al., Curr. Biol. 12:735 (2002); Tuschl et al., Nature Biotechnol. 20:446 (2002); Tuschl, Chembiochem. 2:239 (2001); Harborth et al., J. Cell Sci. 114:4557 (2001); et al., EMBO J. 20:6877 (2001); Lagos-Quintana et al., Science 294:8538 (2001); Hutvagner et al., loc cit, 834; Elbashir et al., Nature 411:494 (2001).

Also within the scope of this invention is the starch resulting from mutants wherein the mutant wx and/or su2 alleles have been moved to another portion of the plant genome by translocation, inversion, or any other methods of chromosome engineering. In addition, starch extracted from a plant grown from artificial mutations and variations of the above genetic composition which may be produced by known standard methods of mutation breeding is also applicable herein.

Also within the scope of this invention is the starch produced from plants other than corn plants, as long as the starch producing plants have a mutant ortholog of the maize GBSSI gene that has intermediate GBSSI activity, and a recessive mutant ortholog of the maize SSIIa gene. In some embodiments, the plants can be wheat, tapioca, rice, cassava, sago, potato, or sorghum.

In some embodiments, the ortholog GBSSI gene in plants other than maize encodes a protein having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more identity to SEQ ID NO: 1, and have the GBSSI activity. In some embodiments, the ortholog has the sequence of UniProt entry number O82627 (*Antirrhinum majus* (Garden snapdragon)), P12615 (*Avena sativa* (Oat)), Q42968 (*Oryza glaberrima* (African rice)), Q43784 (*Manihot esculenta* (Cassava)), POC585 (*Oryza sativa* (Rice)), Q00775 (*Solanum tuberosum* (Potato)), P27736 (*Triticum aestivum* (Wheat)), Q43134 (*Sorghum bicolor* (Sorghum)), Q43092 (*Pisum sativum* (Garden pea)), P84766 (*Aegilops tauschii* subsp. *strangulata* (Goatgrass)), QODEV5 (*Oryza sativa* subsp. *japonica* (Rice)), Q42857 (*Ipomoea batatas* (Sweet potato), P84633 (*Fagopyrum esculentum* (Common buckwheat)), P84765 (*Secale cereale* (Rye)), Q9MAQ0 (*Arabidopsis thaliana*), P09842 (*Hordeum vulgare* (Barley), or A2Y8X2 (*Oryza sativa* subsp. *indica* (Rice)), each of which is herein incorporated by reference in its entirety.

In some embodiments, the ortholog SSIIa gene in plants other than maize encodes a protein having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more identity to SEQ ID NO: 2, and have the SSIIa activity. In some embodiments, the ortholog has the sequence of UniProt entry number V6BPG5 (*Triticum urartu* (Red wild einkorn)), V6BPN2 (*Triticum monococcum* subsp. *Monococcum*), C3W8L4 (*Hordeum vulgare* var. *distichum* (Domesticated barley)), E2GHR4 (*Oryza sativa* subsp. *indica* (Rice)), or E2GHR6 (*Oryza sativa* subsp. *japonica* (Rice)), each of which is herein incorporated by reference in its entirety.

In some embodiments, to produce double mutant plants having the intermediate wx mutant and the recessive su2 mutant, a cross pollination between a plant having the intermediate wx mutant and a plant having the recessive su2 mutant can be made.

For example, a cross pollination can be made between a homozygous wxS mutant (wxSwxSSU2SU2) or a heterozygous wxS mutant (wxSWxSU2SU2) and a homozygous waxy su2 mutant (wxwxsu2su2) or a heterozygous waxy su2 mutant (wxWxsu2su2 or wxwxSU2su2). After the cross, self pollination of the F1 generation having the genotype of wxSwxSU2su2 can be used to generate the F2 plants. Plants having either zero, one, two, or three doses of the wxS gene in the endosperm, and three doses of the recessive su2 gene can be isolated accordingly (e.g., endosperm having the genotype of wxwxwxsu2su2su2, wxSwxwxsu2su2su2, wxSwxSwxsu2su2su2, or wxSwxSwSsu2su2su2). This is only one example of the breeding method, and other breeding schemes can be used, and are within the scope of the present invention.

In some embodiments, field production of plants with endosperms that have at least one dose of the intermediate waxy allele and the recessive sugary-2 allele is carried out by crossing female maize plants with male maize plants. A typical planting arrangement is one male row to several female rows. The female rows are either detasseled or rendered male sterile through various other means known in the art such as cytoplasmic or genetic means.

The starch utilized in this invention may be obtained from inbred lines, or the starch can be obtained from hybrids derived from inbreds containing the intermediate waxy/recessive su2 double mutant. While maize is the exemplary plant herein for the source of the waxy starch, the invention is also applicable to other plant species such as, for example, waxy rice, waxy barley and waxy sorghum, provided that they have an intermediate waxy gene and a recessive su2 gene.

Breeding Methods

To make the plants of the present invention, suitable breeding or selection methods can be used. Popular selection methods commonly include pedigree selection, modified pedigree selection, mass selection, recurrent selection, and backcross breeding.

Open-Pollinated Populations.

The improvement of open-pollinated populations of such crops as rye, many maizes and sugar beets, herbage grasses, legumes such as alfalfa and clover, and tropical tree crops such as cacao, coconuts, oil palm and some rubber, depends essentially upon changing gene-frequencies towards fixation of favorable alleles while maintaining a high (but far from maximal) degree of heterozygosity. Uniformity in such populations is impossible and trueness-to-type in an open-pollinated variety is a statistical feature of the population as a whole, not a characteristic of individual plants. Thus, the heterogeneity of open-pollinated populations contrasts with the homogeneity (or virtually so) of inbred lines, clones and hybrids.

Population improvement methods fall naturally into two groups, those based on purely phenotypic selection, normally called mass selection, and those based on selection with progeny testing. Interpopulation improvement utilizes the concept of open breeding populations; allowing genes to flow from one population to another. Plants in one population (cultivar, strain, ecotype, or any germplasm source) are crossed either naturally (e.g., by wind) or by hand or by bees (commonly *Apis mellifera* L. or *Megachile rotundata* F.) with plants from other populations. Selection is applied to improve one (or sometimes both) population(s) by isolating plants with desirable traits from both sources.

There are basically two primary methods of open-pollinated population improvement. First, there is the situation in which a population is changed en masse by a chosen selection procedure. The outcome is an improved population that is indefinitely propagable by random-mating within itself in isolation. Second, the synthetic variety attains the same end result as population improvement but is not itself propagable as such; it has to be reconstructed from parental lines or clones. These plant breeding procedures for improving open-pollinated populations are well known to those skilled in the art and comprehensive reviews of breeding procedures routinely used for improving cross-pollinated plants are provided in numerous texts and articles, including: Allard, *Principles of Plant Breeding*, John Wiley & Sons, Inc. (1960); Simmonds, *Principles of Crop Improvement*, Longman Group Limited (1979); Hallauer and Miranda, *Quantitative Genetics in Maize Breeding*, Iowa State University Press (1981); and, Jensen, *Plant Breeding Methodology*, John Wiley & Sons, Inc. (1988).

Mass Selection.

In mass selection, desirable individual plants are chosen, harvested, and the seed composited without progeny testing to produce the following generation. Since selection is based on the maternal parent only, and there is no control over pollination, mass selection amounts to a form of random mating with selection. As stated herein, the purpose of mass selection is to increase the proportion of superior genotypes in the population.

Synthetics.

A synthetic variety is produced by crossing inter se a number of genotypes selected for good combining ability in all possible hybrid combinations, with subsequent maintenance of the variety by open pollination. Whether parents are (more or less inbred) seed-propagated lines, as in some sugar beet and beans (*Vicia*) or clones, as in herbage grasses, clovers and alfalfa, makes no difference in principle. Parents are selected on general combining ability, sometimes by test crosses or topcrosses, more generally by polycrosses. Parental seed lines may be deliberately inbred (e.g. by selfing or sib crossing). However, even if the parents are not deliberately inbred, selection within lines during line maintenance will ensure that some inbreeding occurs. Clonal parents will, of course, remain unchanged and highly heterozygous.

Whether a synthetic can go straight from the parental seed production plot to the farmer or must first undergo one or two cycles of multiplication depends on seed production and the scale of demand for seed. In practice, grasses and clovers are generally multiplied once or twice and are thus considerably removed from the original synthetic.

While mass selection is sometimes used, progeny testing is generally preferred for polycrosses, because of their operational simplicity and obvious relevance to the objective, namely exploitation of general combining ability in a synthetic.

The number of parental lines or clones that enter a synthetic vary widely. In practice, numbers of parental lines range from 10 to several hundred, with 100-200 being the average. Broad based synthetics formed from 100 or more clones would be expected to be more stable during seed multiplication than narrow based synthetics.

Pedigreed Varieties.

A pedigreed variety is a superior genotype developed from selection of individual plants out of a segregating population followed by propagation and seed increase of self pollinated offspring and careful testing of the genotype over several generations. This is an open pollinated method that works well with naturally self pollinating species. This method can be used in combination with mass selection in variety development. Variations in pedigree and mass selection in combination are the most common methods for generating varieties in self pollinated crops.

Hybrids.

A hybrid is an individual plant resulting from a cross between parents of differing genotypes. Commercial hybrids are now used extensively in many crops, including corn (maize), sorghum, sugarbeet, sunflower and broccoli. Hybrids can be formed in a number of different ways, including by crossing two parents directly (single cross hybrids), by crossing a single cross hybrid with another parent (three-way or triple cross hybrids), or by crossing two different hybrids (four-way or double cross hybrids).

Pedigree Selection.

Pedigree breeding is used commonly for the improvement of self-pollinating crops or inbred lines of cross-pollinating crops. Two parents possessing favorable, complementary traits are crossed to produce an $F_1$. An $F_2$ population is produced by selfing one or several $F_1$s or by intercrossing two $F_1$s (sib mating). The dihaploid breeding method or other ploidy reduction techniques could also be used. Selection of the best individuals is usually begun in the $F_2$ population; then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release of new cultivars. Similarly, the development of new cultivars through the dihaploid system requires the selection of the cultivars followed by two to five years of testing in replicated plots.

Backcross Breeding.

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are, selected and repeatedly crossed (backcrossed) to the recurrent parent. The resulting plant is expected to have the attributes of the recurrent parent (e.g., cultivar) and the desirable trait transferred from the donor parent.

Bulk Segregation Analysis (BSA).

BSA, a.k.a. bulked segregation analysis, or bulk segregant analysis, is a method described by Michelmore et al. (Michelmore et al., 1991, Identification of markers linked to disease-resistance genes by bulked segregant analysis: a rapid method to detect markets in specific genomic regions by using segregating populations. *Proceedings of the National Academy of Sciences, USA*, 99:9828-9832) and Quarrie et al. (Quarrie et al., 1999, *Journal of Experimental Botany*, 50(337):1299-1306).

For BSA of a trait of interest, parental lines with certain different phenotypes are chosen and crossed to generate F2, doubled haploid or recombinant inbred populations with QTL analysis. The population is then phenotyped to identify individual plants or lines having high or low expression of the trait. Two DNA bulks are prepared, one from the individuals having one phenotype (e.g., resistant to virus), and the other from the individuals having reversed phenotype (e.g., susceptible to virus), and analyzed for allele frequency with molecular markers. Only a few individuals are required in each bulk (e.g., 10 plants each) if the markers are dominant (e.g., RAPDs). More individuals are needed when markers are co-dominant (e.g., RFLPs). Markers linked to the phenotype can be identified and used for breeding or QTL mapping.

Targeting Induced Local Lesions in Genomes (TILLING®).

Breeding schemes of the present application can include crosses with TILLING® plant cultivars. TILLING® is a method in molecular biology that allows directed identification of mutations in a specific gene. TILLING® was introduced in 2000, using the model plant *Arabidopsis thaliana*. TILLING® has since been used as a reverse genetics method in other organisms such as zebrafish, corn, wheat, rice, soybean, tomato and *Brassica rapa* var. *nipposinica*.

The method combines a standard and efficient technique of mutagenesis with a chemical mutagen (e.g., Ethyl methanesulfonate (EMS)) with a sensitive DNA screening-technique that identifies single base mutations (also called point mutations) in a target gene. EcoTILLING is a method that uses TILLING® techniques to look for natural mutations in individuals, usually for population genetics analysis (see Comai, et al., 2003 The Plant Journal 37, 778-786; Gilchrist et al. 2006 Mol. Ecol. 15, 1367-1378; Mejlhede et al. 2006 Plant Breeding 125, 461-467; Nieto et al. 2007 BMC Plant Biology 7, 34 42, each of which is incorporated by reference hereby for all purposes). DEcoTILLING is a modification of TILLING® and EcoTILLING which uses an inexpensive method to identify fragments (Garvin et al., 2007, DEcoTILLING: An inexpensive method for SNP discovery that reduces ascertainment bias. Molecular Ecology Notes 7, 735-746).

The TILLING® method relies on the formation of heteroduplexes that are formed when multiple alleles (which could be from a heterozygote or a pool of multiple homozygotes and heterozygotes) are amplified in a PCR, heated, and then slowly cooled. A "bubble" forms at the mismatch of the two DNA strands (the induced mutation in TILLING® or the natural mutation or SNP in EcoTILLING), which is then cleaved by single stranded nucleases. The products are then separated by size on several different platforms.

More detailed description on methods and compositions on TILLING® can be found in U.S. Pat. No. 5,994,075, US 2004/0053236 A1, WO 2005/055704, and WO 2005/048692, each of which is hereby incorporated by reference for all purposes.

Thus in some embodiments, the breeding methods of the present disclosure include breeding with one or more TILLING® plant lines with one or more identified mutations.

Mutation Breeding.

Mutation breeding is another method of introducing new traits into plants. Mutations that occur spontaneously or are artificially induced can be useful sources of variability for a plant breeder. The goal of artificial mutagenesis is to increase the rate of mutation for a desired characteristic. Mutation rates can be increased by many different means or mutating agents including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid or acridines. Once a desired trait is observed through mutagenesis the trait may then be incorporated into existing germplasm by traditional breeding techniques. Details of mutation breeding can be found in W. R. Fehr, 1993, Principles of Cultivar Development, Macmillan Publishing Co. New breeding techniques such as the ones involving the uses of Zinc Finger Nucleases or oligonucleotide directed mutagenesis shall also be used to generate genetic variability and introduce new trails into varieties.

In some embodiments, the mutation breeding comprises a single locus conversion. A single locus may contain several genes and/or transgenes, such as a transgene for disease resistance that, in the same expression vector, also contains a transgene for herbicide resistance. The gene for herbicide resistance may be used as a selectable marker and/or as a phenotypic trait. A single locus conversion of site specific integration system allows for the integration of multiple genes at the converted locus. A single locus conversion also allows for making one or more site specific changes to the plant genome. In some embodiments, the single locus conversion is performed by genome editing, a.k.a. genome editing with engineered nucleases (GEEN). In some embodiments, the genome editing comprises using one or more engineered nucleases. In some embodiments, the engineered nucleases include, but are not limited to Zinc finger nucleases (ZFNs), Transcription Activator-Like Effector Nucleases (TALENs), the CRISPR/Cas system, and engineered meganuclease re-engineered homing endonucleases. In some embodiments, the single locus conversion changes one or several nucleic acids of the plant genome.

Double Haploids and Chromosome Doubling.

One way to obtain homozygous plants without the need to cross two parental lines followed by a long selection of the segregating progeny, and/or multiple back-crossings is to produce haploids and then double the chromosomes to form doubled haploids. Haploid plants can occur spontaneously, or may be artificially induced via chemical treatments or by crossing plants with inducer lines (Seymour et al. 2012, PNAS vol 109, pg 4227-4232; Zhang et al., 2008 Plant Cell Rep. December 27(12) 1851-60). The production of haploid progeny can occur via a variety of mechanisms which can affect the distribution of chromosomes during gamete formation. The chromosome complements of haploids sometimes double spontaneously to produce homozygous doubled haploids (DHs). Mixoploids, which are plants which contain cells having different ploidies, can sometimes arise and may represent plants that are undergoing chromosome doubling so as to spontaneously produce doubled haploid tissues, organs, shoots, floral parts or plants. Another common technique is to induce the formation of double haploid plants with a chromosome doubling treatment such as colchicine (El-Hennawy et al., 2011 Vol 56, issue 2 pg 63-72; Doubled Haploid Production in Crop Plants 2003 edited by Maluszynski ISBN 1-4020-1544-5). The production of doubled haploid plants yields highly uniform cultivars and is especially desirable as an alternative to sexual inbreeding of longer-generation crops. By producing doubled haploid progeny, the number of possible gene combinations for inherited traits is more manageable. Thus, an efficient doubled haploid technology can significantly reduce the time and the cost of inbred and cultivar development.

Protoplast Fusion.

In another method for breeding plants, protoplast fusion can also be used for the transfer of trait-conferring genomic material from a donor plant to a recipient plant. Protoplast fusion is an induced or spontaneous union, such as a somatic hybridization, between two or more protoplasts (cells of which the cell walls are removed by enzymatic treatment) to produce a single bi- or multi-nucleate cell. The fused cell that may even be obtained with plant species that cannot be interbred in nature is tissue cultured into a hybrid plant exhibiting the desirable combination of traits.

Tissue Culture.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, leaves, stems, roots, root tips, anthers, pistils, meristematic cells, axillary buds, ovaries, seed coat, endosperm, hypocotyls, cotyledons and the like. Means for preparing and maintaining plant tissue culture are well known in the art. By way of example, a tissue culture comprising organs has been used to produce regenerated plants. U.S. Pat. Nos. 5,959,185, 5,973,234, and 5,977,445 describe certain techniques, the disclosures of which are incorporated herein by reference.

This invention is further illustrated by the following examples which should not be construed as limiting. The contents of all references, patents and published patent applications cited throughout this application, as well as the Figures and the Sequence Listing, are incorporated herein by reference.

Example 1

Generating Grain with 1, 2, or 3 Doses of the wxS Allele

Because of the triploid nature of the corn endosperm, wherein two polar nuclei from the maternal parent are fertilized by one sperm cell from the paternal parent, three genotypic combinations are possible. Using a wxSwxSsu2su2 plant as a female, pollinated by a wxwxsu2su2 male results in 'dose-2' or wxSwxSwxsu2su2su2 grain. Using the wxSwxSsu2su2 as a male, pollinating a wxwxsu2su2 female results in 'dose-1' or wxSwxwxsu2su2su2 grain. Self pollination of wxSwxSsu2su2 results in 'dose-3' or wxSwxSwxSsu2su2su2 grain.

| wxS dosage | Endosperm Genotype |
|---|---|
| (1 wxS) | wxSwxwxsu2su2su2 |
| (2 wxS) | wxSwxSwxsu2su2su2 |
| (3 wxS) | wxSwxSwxSsu2su2su2 |
| starch from wxwxwxsu2su2su2 seed (0 wxS) | wxwxwxsu2su2su2 |
| AMIOCA ™ starch (0 wxS) | wxwxwxSU2SU2SU2 |
| starch from wxwxwxSU2su2su2 (0 wxS) | wxwxwxSU2su2su2 |

Example 2

Viscosity of Starch Using a Rapid Visco Amylograph (RVA)

The viscosity of maize starch derived from plants containing 0, 1, 2, and 3 doses of the wxS allele in the recessive sugary-2 mutant plants was determined using a Rapid Visco Amylograph (Newport Scientific, Eden Prairie, Minn.). The AMIOCA™ starch and wxwxwxSU2su2su2 starch are included as checks. The genotype of endosperms from which the starch was isolated is summarized in the table below. The amylose content was measured using Megazyme® amylose kit. The amylose content of the starch increases with the increase of GBSSI activity. The amylose contents of wxwxwxsu2su2su2 starch (7.4%), AMIOCA™ starch (7.1%), and wxwxwxSU2su2su2 starch (6.1%) were lower than Waxy Stonor (12.8%) and wxwxwxsu2su2su2 starch with 1 to 3 doses of wxS gene in the endosperm (8.2-14.6%). The amylose content of wxwxwxsu2su2su2 starch (7.4%, 8.2%, 13.8%, and 14.6%) increased with the increase of wxS dosage (0, 1, 2, and 3 doses of wxS, respectively). The results suggested that the introduction of wxS gene to wxwxwxsu2su2su2 slightly increased amylose content of the starch.

| Sample | Amylose (%) |
|---|---|
| Q3017a (1 wxS) | 8.2 ± 0.1 |
| Q8412a (2 wxS) | 13.8 ± 0.0 |
| Q7738a (3 wxS) | 14.6 ± 0.1 |
| wxwxwxsu2su2su2 starch (0 wxS) | 7.4 ± 0.1 |
| K5594a (Waxy Stonor) | 12.8 ± 0.1 |
| AMIOCA ™ starch | 7.1 ± 0.0 |
| wxwxwxSU2su2su2 starch | 6.1 ± 0.1 |

Pasting property of waxy corn starch was analyzed using a Rapid Visco-Analyzer (RVA, Newport Scientific, Sydney, Australia) using "Standard 2" profile method. A suspension (28.0 g) containing 8% starch (w/w, dry starch basis, dsb) was equilibrated at 50° C. for 1 min, heated to 95° C. at a rate of 6° C./min, held at 95° C. for 5 min, and then cooled to 50° C. at a rate of 6° C./min. The rotating speed for the paddle was 160 rpm except that 960 rpm was used for the first 10 s. The results are shown in FIG. 1 and FIG. 2. The existing wxwxwxsu2su2su2 starch had the lowest pasting temperature, peak viscosity, and final viscosity. After introduction of wxS gene to wxwxwxsu2su2su2 starch, the starch samples (Q3017a [1 wxS], Q8412a [2 wxS], and Q7738a [3 wxS]) showed increased peak viscosity compared to the existing wxwxwxsu2su2su2 starch (0 wxS). However, only the wxSwxwxsu2su2su2 starch with one dose of wxS gene showed the peak viscosity much higher than Waxy Stonor, AMIOCA™ starch, and wxwxwxSU2su2su2 starch.

The results indicate that improvement in pasting temperature will allow starch extraction via the wet-milling process.

Example 3

Freeze-Thaw Stability of Starch

Figure 3:
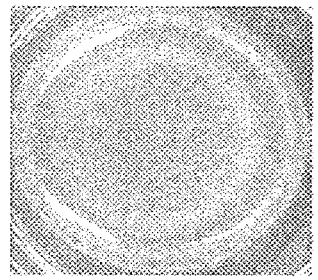
FIG. 3 depicts the freeze-thaw stability test of starch of waxy-sugary 2 double-mutant plants with one, two, three, or zero doses of wxS gene, starch from Waxy Stonor seed, wxwxwxSU2su2su2 starch, and AMIOCA™ starch. The above-stated starches are presented in rows, and illustrative images of starch gels are provided after the first freeze-thaw (Cycle 1), after the third freeze-thaw (Cycle 3), and after the fifth freeze-thaw (Cycle 5).
Figure 3:
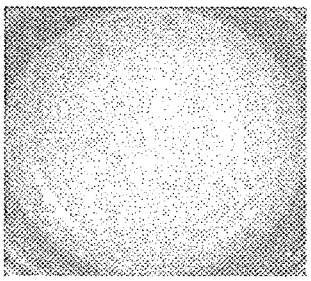
Figure 3:
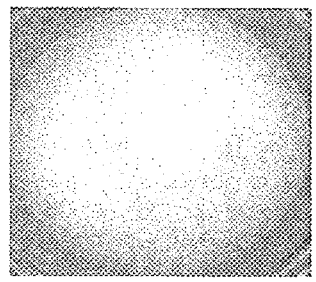
Figure 3:
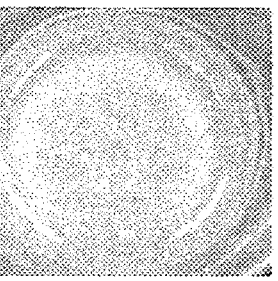

The maize starch derived from plants containing 0, 1, 2, and 3 doses of the wxS allele in the recessive sugary-2 mutant plants was tested for freeze-thaw stability. AMIOCA™ starch and wxwxwxSU2su2su2 starch were included as checks. Starch samples 8% solids were cooked in a water bath at 95° C. for 20 minutes. The starch slurry was mixed with a glass rod for three minutes followed by quiescent heating for 17 minutes during cooking. Freeze-thaw stability of starch gel (8%, w/w) at neutral pH was analyzed using a Caron cycling freezer for five freeze-thaw cycles. In each cycle, the sample was frozen for 6 hours and thawed for 6 hours with 2 cycles/day. The samples were visually inspected for syneresis, both on the surface and when pressed, as well as for opacity and gelling changes. This freeze-thaw cycle was repeated. The results are shown in FIG. 3. After first freeze/thaw cycle, only Waxy Stonor starch gel showed high opacity, indicating high degree of starch retrogradation. The opacity of starch gel increased with the increase of freeze/thaw cycles. At third freeze/thaw cycle, the starch gels of AMIOCA™ starch, wxwxwxSU2su2su2 starch, and Waxy Stonor became very opaque, whereas the starch gels of Q3017a (1 wxS), Q8412a (2 wxS), Q7738a (3 wxS), and existing wxwxwxsu2su2su2 starch were still not opaque. After five freeze/thaw cycles, Q3017a (1 wxS), Q8412a (2 wxS), Q7738a (3 wxS), and existing wxwxwxsu2su2su2 starch become slightly opaque.

The results suggested that the slight increase of amylose in starch samples had little effect in the freeze/thaw stability. The Q3017a (1 wxS), Q8412a (2 wxS), Q7738a (3 wxS) starches had freeze/thaw stability better than wxwxwxSU2su2su2 starch and AMIOCA™ starch.

Example 4

Differential Scanning Calorimetry (DSC) Test

Thermal properties of maize starch derived from plants containing 0, 1, 2, and 3 doses of the wxS allele in the recessive sugary-2 mutant plants were determined using Differential Scanning Calorimetry (DSC). The AMIOCA™ starch and wxwxwxSU2su2su2 starch were included as checks. Differential Scanning Calorimetry (DSC) measures heat absorbed or given off by a sample in a controlled atmosphere at specified temperatures. DSC provides information about a specific heat and latent heat of samples as temperature rises, which indicates changes in the amorphous and crystalline structures. Data is recorded in terms of heat flow, and is presented in joules/gram (J/g) (Cassel, 2002). In the analysis of starch, starch gelatinization parameters such as peak onset, peak temperature, end of peak, and gelatinization enthalpy change information were collected. The results are shown in FIG. 4. wxSwxwxsu2su2su2 starch (Q3017a), wxSwxSwxsu2su2su2 starch (Q8412a), wxSwxSwxSsu2su2su2 starch (Q7738a), and wxwxwxsu2su2su2 starch (0 wxS) showed lower gelatinization temperatures than AMIOCA™ starch, Waxy Stonor, and wxwxwxSU2su2su2 starch, which is consistent with the better freeze/thaw stability of the starch isolated from endosperm of maize with one, two, and three doses of wxS. The wxSwxwxsu2su2su2 starch with one dose of wxS (Q3017a) had slightly higher onset gelatinization temperature than other hybrids (Q8412a [2 wxS], Q7738a [3 wxS], and wxwxwxsu2su2su2 starch), indicating that the Q3017a had better wet milling characteristics than other hybrids.

Example 5

Starch Granule

Figure 5:
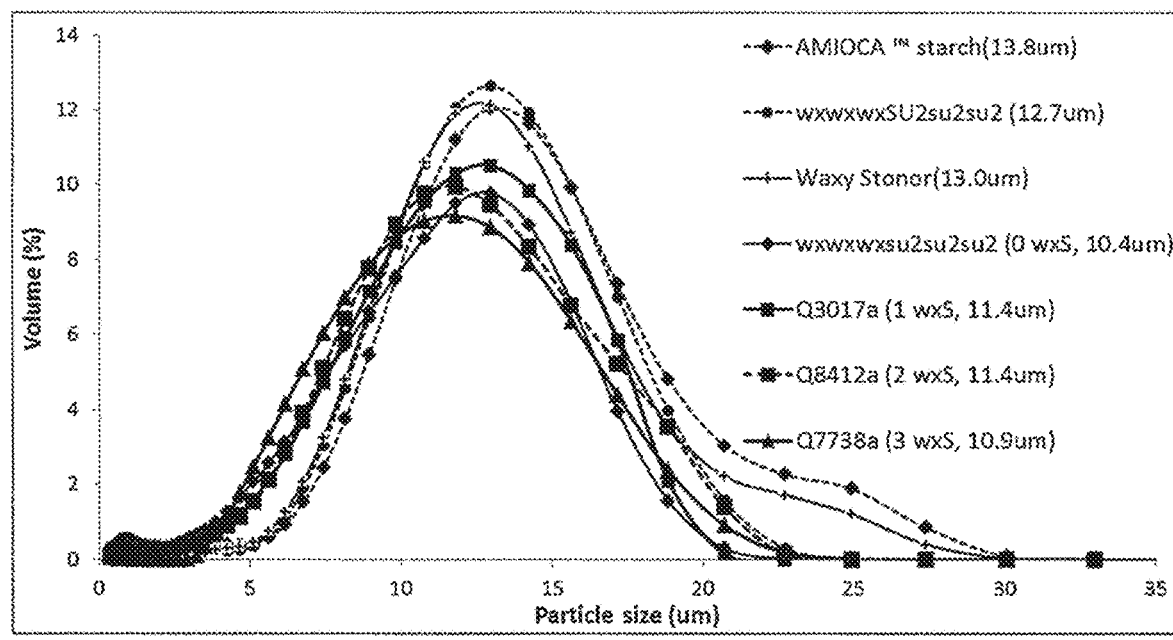
FIG. 5 depicts the granule size distribution of starch of AMIOCA™ starch, wxwxwxSU2su2su2 starch, and starch of waxy-sugary 2 double-mutant plants with zero, one, two, or three doses of wxS gene.
Figure 6:
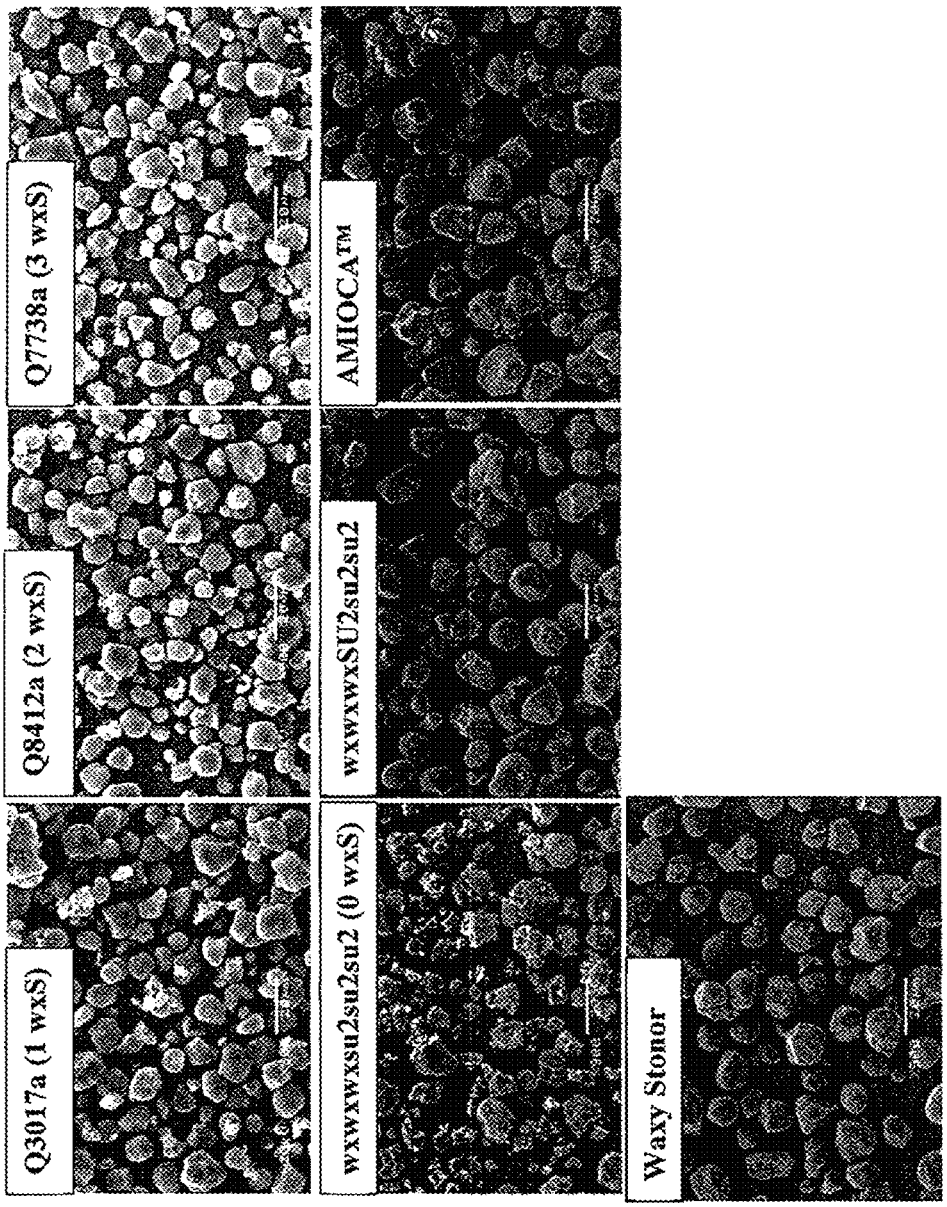
FIG. 6 depicts the granule morphology of starch of waxy-sugary 2 double-mutant plants with one, two, three, or zero doses of wxS gene, wxwxwxSU2su2su2 starch, AMIOCA™ starch, and starch from Waxy Stonor seed. Illustrative images for each of the above-referenced starches captured using a scanning electron microscope are provided.

The average particle size of waxy maize starch derived from plants containing 1, 2, and 3 doses of the wxS allele in the recessive sugary-2 mutant plants was measured by laser light scattering. The AMIOCA™ starch and wxwxwxSU2su2su2 starch were included as checks. The results are shown in FIG. 5. In addition, the Scanning electron micrograph of each sample was provided in FIG. 6 to show granule morphology. The average starch granule sizes of Q3017a (11.4 μm), Q8412a (11.4 μm), and Q7738a (10.9 μm) were larger than the existing wxwxwxsu2su2su2 starch (10.4 μm), suggesting that the introduction of wxS gene to Waxy VO increased the starch granule size. The result was consistent with the SEM images (FIG. 5) showing that the introduction of wxS gene to wxwxwxsu2su2su2 starch increased the starch granule integrity.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present disclosure, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present disclosure is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

```
                         Sequence Listing

SEQ ID NO: 1 Waxy Protein in maize
        10          20          30          40          50
MAALATSQLV  ATRAGLGVPD  ASTFRRGAAQ  GLRGARASAA  ADTLSMRTSA 60          70          80          90         100
RAAPRHQQQA  RRGGRFPSLV  VCASAGMNVV  FVGAEMAPWS  KTGGLGDVLG 110         120         130         140         150
GLPPAMAANG  HRVMVVSPRY  DQYKDAWDTS  VVSEIKMGDG  YETVRFFHCY
```

Sequence Listing 160        170        180        190        200
KRGVDRVFVD HPLFLERVWG KTERKTYGPV ACTDYRDNQL RFSLLCQAAL 210        220        230        240        250
EAPRILSLNN NPYFSGPYGE DVVFVCNDWH TGPLSCYLKS NYQSHGIYRD 260        270        280        290        300
AKTAFCIHNI SYQGRFAFSD YPELNLPERF KSSFDFIDGY EKPVEGRKIN 310        320        330        340        350
WMKAGILEAD RvLTVSPYYA EELISGIARG CELDNIMRLT GITGIVNGMD 360        370        380       390v  400
VSEWDPSRDK YIAVKYDVST AVEAKALNKE ALQAEVGLPV DRNIPLVAFI 410        420        430        440        450
GRLEEQKGPD VMAAAIPQLM EMVEDVQIVL LGTGKKKFER MLMSAEEKFP 460        470        480        490        500
GKVRAVVKFN AALAHHIMAG ADVLAVTSRF EPCGLIQLQG MRYGTPCACA 510        520        530        540        550
STGGLVDTII EGKTGFHMGR LSVDCNVVEP ADVKKVATTL QRAIKVVGTP 560        570        580        590        600
AYEEMVRNCM IQDLSWKGPA KNWENVLLSL GVAGGEPGVE GEEIAPLAKE

NVAAP

SEQ ID NO: 2 Sugary 2 Protein in maize
         10         20         30         40         50
MSSAAVSSSS STFFLALASA SPGGRRRARV GSSPFHTGAS LSFAFWAPPS 60         70         80         90        100
PPRAPRDAAL VRAEAEAGGK DAPPERSGDA ARLPRARRNA VSKRRDPLQP 110        120        130        140        150
VGRYGSATGN TARTGAASCQ NAALADVEIK SIVAAPPTSI VKFPAPGYRM 160        170        180        190        200
ILPSGDIAPE TVLPAPKPLH ESPAVDGDSN GIAPPTVEPL VQEATWDFKK 210        220        230        240        250
YIGFDEPDEA KODSRVGADD AGSFEHYCDN D3GPLAGENV MNVIVVAAEC 260        270        280        290        300
SPWCKTGGLG DVVCALPKAL ARRGHRVMVV VPRYGDYVEA FDMGIRKYYK 310        320        330        340        350
AAGPVNYFHA FIDGVDFVFI DAPLFRHRQD DIYGGSRQEI MKRMILFCKV 360        370        380       390v  400
AVEVPWHVPC GGVCYGDGNL VFIANDWHTA LLPVYLKAYY RDHGLMQYTR 410        420        430        440        450
GVLVTHNIAH WRGPVDEFP YMDLPEHYLQ HFELYDPVGG EHANIFAAGL 460        470        480        490        500
KMADRVVTVS RGYLWELKTV EGGWGLHDII RSNDWKINGI VNGIDHQEWN 510        520        530        540        550
PKVDVHLRSD GYTNYSLETL DAGKROCKAA LQRELGLEVR DDVPLLGFIG 560        570        580        590        600
RLDGQKGVDI IGDAMPWIAG QDVQLVMLGT GRADLERMLQ HLEREHPNKV 610        620        630        640        650
RGWVGFSVPM AHRITAGADV LVMPSRFEPC GLNQLYAMAY GTVPVVHAVG 660        670        680        690        700
GLRDTVAPFD PFSDAGLGWT FDRAEANKLI EALRHCLDTY RNYEESWKSL 710        720
QARGMSQDLS WDHAAELYED VLVKAKYQW

What is claimed is:

1. A double-mutant corn plant, wherein the corn plant is homozygous recessive for a starch synthase IIa (su2) gene, and either homozygous or heterozygous for a mutated Granule-bound starch synthase I (GBSSI) gene, wherein the double-mutant corn plant has a phenotype in which the mutated GBSSI gene has less GBSSI activity than a wild type GBSSI gene (Wx), but has higher GBSSI activity than a recessive, loss-of-function GBSSI gene (wx).

2. The double-mutant corn plant of claim 1, wherein the mutated GBSSI gene is the wx-Stonor (wxS) allele.

3. The double-mutant corn plant of claim 1, wherein the plant is generated by cross pollination of a first corn plant having a genotype of wxwxsu2su2, and a second corn plant having a genotype of wxSwxSsu2su2 or a genotype of wxSwxsu2su2.

4. The double-mutant corn plant of claim 1, producing a corn seed having an endosperm wherein the endosperm of the corn seed has one dose, two doses, or three doses of a wxS allele, and wherein the endosperm has a genotype of wxSwxwxsu2su2su2, wxSwxSwxsu2su2su2, or wxSwxSwxSsu2su2su2.

5. The double-mutant corn plant of claim 1, producing a corn seed comprising an endosperm having starch wherein the starch produced in the endosperm of the corn plant has a higher pasting temperature compared to a starch produced in an endosperm of a double, waxy sugary-2 recessive mutant corn plant having a genotype of wxwxwxsu2su2su2.

6. A seed of the double-mutant corn plant of claim 1.

7. A plant part, plant cell, or tissue culture of the double-mutant corn plant of claim 1.

8. The plant part of claim 7, wherein the plant part is selected from the group consisting of an endosperm, a leaf, a flower, an ovule, a pollen, a rootstock, and a scion.

9. A method for producing starch comprising obtaining starch from an endosperm of a corn seed wherein the corn seed is from double-mutant corn plant of claim 1.

10. A method for producing starch comprising growing the double-mutant corn plant of claim 1, and harvesting seeds from the double-mutant corn plant.

11. A method for producing a corn seed comprising crossing a first parent corn plant with a second parent corn plant and harvesting the resultant corn seed, wherein said first parent corn plant and/or second parent corn plant is the double-mutant corn plant of claim 1.

12. The method of claim 11 wherein producing a corn seed comprises self-pollinating the double-mutant corn plant of claim 1 and harvesting the resultant corn seed.

13. A method of vegetatively propagating the corn plant of claim 1, said method comprising collecting a part of the plant of claim 1 and regenerating a plant from said part.

14. A method of producing a corn plant derived from the double-mutant corn plant of claim 1, the method comprising self-pollinating the double-mutant plant of claim 1 at least once to produce a progeny plant derived from the double-mutant plant of claim 1.

15. A method of producing a corn plant derived from the double-mutant plant of claim 1, the method comprising crossing the double-mutant plant of claim 1 with a second corn plant to produce a progeny plant of the double-mutant plant of claim 1.

16. A method of producing a corn plant having the phenotype of the double-mutant plant of claim 1 comprising obtaining one of a first plant, plant part, plant cell, or tissue culture and introducing a transgene into the first plant or plant, plant cell or tissue culture to obtain a modified plant material, and using the modified plant material to obtain the corn plant having the phenotype of the double-mutant plant of claim 1, wherein the transgene confers the phenotype of the double-mutant plant of claim 1 to the corn plant.

17. A method of producing a corn plant having the phenotype of the double-mutant plant of claim 1 comprising obtaining one of a first plant, plant part, plant cell, or tissue culture and gene-editing the first plant, plant part, plant cell, or tissue culture to obtain a modified plant material, and using the modified plant material to obtain the corn plant having the phenotype of the double-mutant plant of claim 1 wherein the edited gene confers the phenotype of the double-mutant plant of claim 1 to the corn plant.

18. A method of producing a corn plant having the phenotype of the double-mutant plant of claim 1 comprising obtaining one of a first plant, plant part, plant cell, or tissue culture and introducing a mutation into the first plant, plant part, plant cell, or tissue culture the mutation to obtain a modified plant material comprising a mutated genetic sequence, and using the modified plant material to obtain the corn plant having the phenotype of the double-mutant plan of claim 1, wherein the genetic sequence confers the phenotype of the double-mutant plant of claim 1 to the corn plant.

19. A starch extracted from a double mutant corn plant, wherein the double-mutant corn plant is the corn plant of claim 1.

20. The starch of claim 19 wherein the double-mutant corn plant is the corn plant of claim 3.

21. The starch of claim 19 wherein the double-mutant corn plant is the corn plant of claim 4, and wherein the starch is extracted from the endosperm of a seed produced by the double-mutant corn plant of claim 4.

* * * * *